(12) United States Patent
Villafranca et al.

(10) Patent No.: US 11,938,104 B1
(45) Date of Patent: Mar. 26, 2024

(54) COMPOSITIONS AND METHODS FOR PREVENTION AND TREATMENT OF CORONAVIRUS AND RELATED DISORDERS

(71) Applicant: Abrexa Pharmaceuticals, Inc., San Diego, CA (US)

(72) Inventors: Jesus E. Villafranca, San Diego, CA (US); Charles Richard Kissinger, San Diego, CA (US)

(73) Assignee: ABREXA PHARMACEUTICALS, INC., San Diego, CA (US)

( * ) Notice: Subject to any disclaimer, the term of this patent is extended or adjusted under 35 U.S.C. 154(b) by 0 days.

(21) Appl. No.: 17/573,503

(22) Filed: Jan. 11, 2022

Related U.S. Application Data

(60) Provisional application No. 63/135,875, filed on Jan. 11, 2021.

(51) Int. Cl.
| | |
|---|---|
| A61K 31/167 | (2006.01) |
| A61K 31/4365 | (2006.01) |
| A61K 31/616 | (2006.01) |
| A61K 31/7064 | (2006.01) |
| A61K 31/727 | (2006.01) |
| A61K 38/48 | (2006.01) |
| A61P 7/02 | (2006.01) |

(52) U.S. Cl.
CPC ........ *A61K 31/167* (2013.01); *A61K 31/4365* (2013.01); *A61K 31/616* (2013.01); *A61K 31/7064* (2013.01); *A61K 31/727* (2013.01); *A61K 38/482* (2013.01); *A61P 7/02* (2018.01)

(58) Field of Classification Search
CPC .............................. A61K 31/15; A61P 25/28
See application file for complete search history.

(56) References Cited

U.S. PATENT DOCUMENTS

2010/0305181 A1* 12/2010 Schubert .............. A61K 31/136 564/151

FOREIGN PATENT DOCUMENTS

WO WO-2021222438 A1 * 11/2021 ........... A61K 31/167

OTHER PUBLICATIONS

Wang et al. (J. Thromb Haemost 2020, 18:1752-1755) (Year: 2020).*
Fanne et al (Neuropharmacology 58 (2010) 972-980) (Year: 2010).*
Song et al., "Neuroinvasion of SARS=COV-2 in human and mouse brain", Biorxiv Preprint, Sep. 8, 2020, uploaded from https://doi.org/10.1101/2020.06.25.169946, pp. 1-41.
Zuo et al., "Plasma tissue plasminogen activator and plasminogen activator inhibitor-1 in hospitalized COVID-19 patients", Medrxiv Preprint, Dec. 5, 2020, downloaded from https://doi.org/10.1101/2020.08.29.20184358, pp. 1-23.
Wang et al., Tissue plasminogen activator (tPA) treatment for COVID-a9 associated acute respiratory distress syndrome (ARDS): A case series, International Society on Thrombosis and Haemostasis, Apr. 2020, pp. 1-4.

\* cited by examiner

*Primary Examiner* — Savitha M Rao
(74) *Attorney, Agent, or Firm* — Pillsbury Winthrop Shaw Pittman LLP

(57) ABSTRACT

Presented herein are compositions and methods for preventing, reducing, delaying and treating a coronavirus infection and related disorders such as respiratory distress, disseminated intravascular coagulation, and central nervous system pathologies caused by coronavirus infection.

3 Claims, 8 Drawing Sheets

Suture model: J147 injected immediately after reperfusion

| | J147 | | |
|---|---|---|---|
| Vehicle | 1mg/kg (iv) | 10mg/kg (iv) | 30mg/kg (iP) |

Bederson Scale:   3           3           1           2

Bederson Scale:   5           3           2           3

Fig. 2A  Fig. 2B          Fig. 2C  Fig. 2D
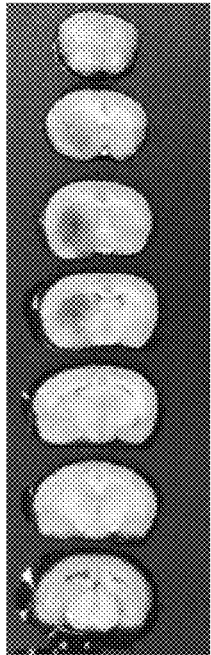 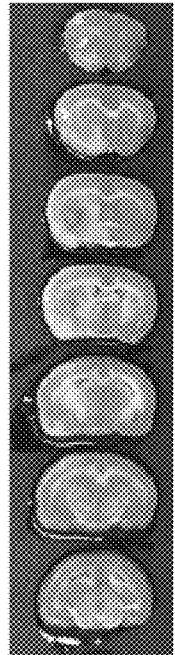   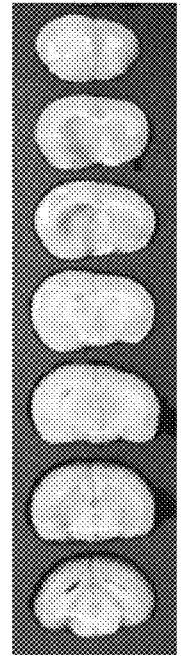 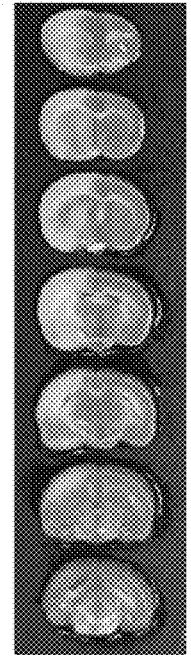
Bederson Scale:   4                        5
Fig. 2E  Fig. 2F          Fig. 2G  Fig. 2H
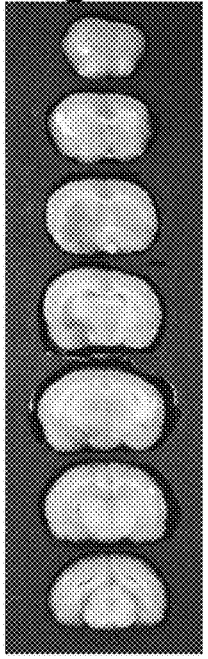 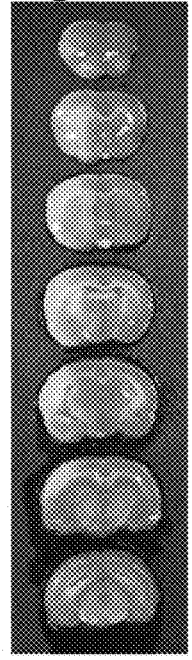   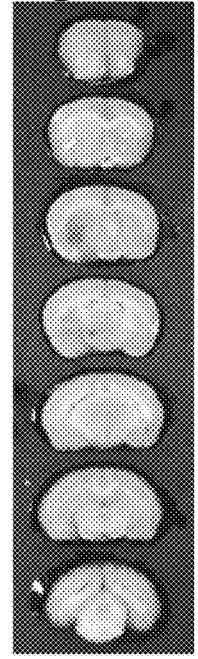 
Bederson Scale:   4                        3
tPA treated: at 4h

Fig. 3A  Fig. 3B          Fig. 3C  Fig. 3D
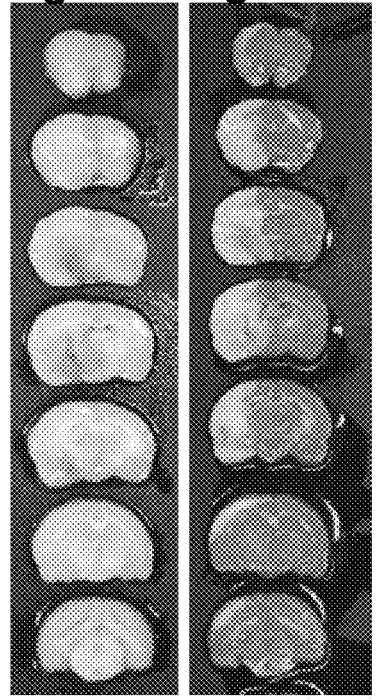
Bederson Scale:  3                      2
Fig. 3E  Fig. 3F          Fig. 3G  Fig. 3H
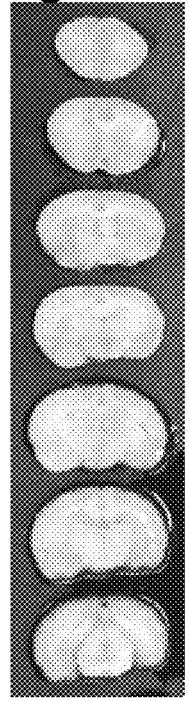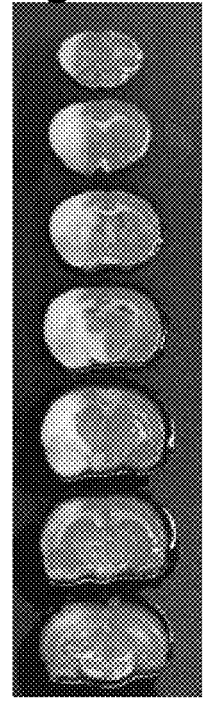   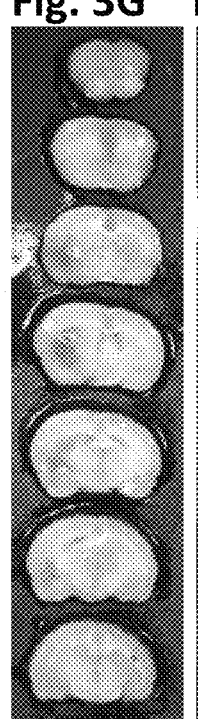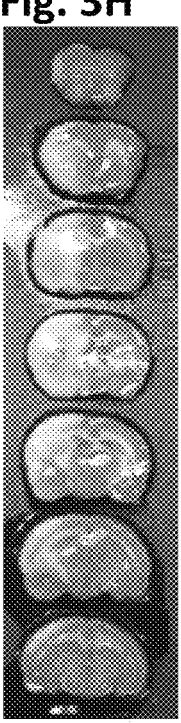
Bederson Scale:  3                      4
tPA + J147: treated at 4h

COMPOSITIONS AND METHODS FOR PREVENTION AND TREATMENT OF CORONAVIRUS AND RELATED DISORDERS

FIELD OF THE INVENTION

Presented herein, in certain embodiments, are methods of preventing, reducing, delaying and treating a coronavirus infection and related disorders such as respiratory distress and disseminated intravascular coagulation. The methods described herein comprise, in part, administering a compound disclosed herein to a subject in need thereof. In some embodiments, a compound described herein is administered in combination with a thrombolytic therapy).

BACKGROUND

COVID-19 is caused by infection of a subject with a coronavirus called SARS-CoV-2. Most patients afflicted with a coronavirus infection experience mild to severe, and even life-threating respiratory distress, such as acute respiratory distress syndrome (ARDS). Prothrombic coagulopathy (blood clotting) is commonly found in patients with coronavirus-induced ARDS and over 70% of patients who die of COVID-19 present with disseminated intravascular coagulation (DIC) often with high venous thromboembolism rates, elevated D-dimer levels, high fibrinogen levels and pulmonary congestion with microvascular thrombosis and occlusion (Wang et al. (2020) J. Thromb. Haemost. 00:1-4).

BRIEF DESCRIPTION OF THE DRAWINGS

The drawings illustrate embodiments of the technology and are not limiting. For clarity and ease of illustration, the drawings are not made to scale and, in some instances, various aspects may be shown exaggerated or enlarged to facilitate an understanding of particular embodiments.

FIG. 1A & FIG. 1B are control animals treated with placebo and showing Bederson Scores 3 and 5, and significant infarct volume (white). FIGS. 1C & 1D are animals treated with 1 mg/kg J147 administered intravascularly (iv), showing better Bederson Scores of 3 and 3, and insignificant reduction in infarct volume relative to placebo. FIGS. 1E & 1F are animals treated with 10 mg/kg iv J147, showing much improved Bederson scores of 1 and 2, and a large reduction of infarct volume. FIGS. 1G & 1H are animals treated with J147 administered intraperitoneally, showing Bederson scores of 2 and 3, and modest reduction of infarct volume.

FIGS. 2A, 2B, 2C, 2D, 2E, 2F, 2G, and 2H show images of brains isolated from animals treated with tPA only and FIGS. 3A, 3B, 3C, 3D, 3E, 3F, 3G, and 3H show images of brains isolated from animals treated with tPA+J147. Representative images of unstained coronal sections (FIGS. 2A, 2C, 2E, 2G & FIGS. 3A, 3C, 3E and 3G) show intracerebral hemorrhage (red color) and TTC-stained coronal sections (FIG. 2B, 2D, 2F, 2H & FIGS. 3B, 3D, 3F and 3H) show tissue infarction (white color) and normal tissue (red color) in the indicated groups 24 hours after stroke.

SUMMARY

Figure 1A:
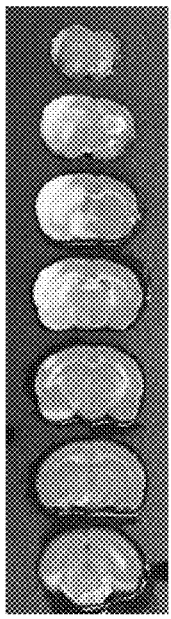
FIGS. 1A, 1B, 1C, 1D, 1E, 1F, 1G, and 1H show representative images (chosen from the median animal in each group) of triphenyl tetrazolium chloride (TTC)-stained brain coronal sections showing tissue infarction (white color) and normal tissue (red color) in the indicated groups 24 hours after stroke.
Figure 1C:
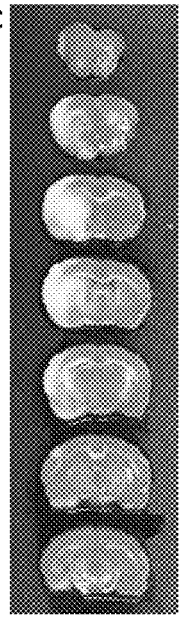
Figure 1E:
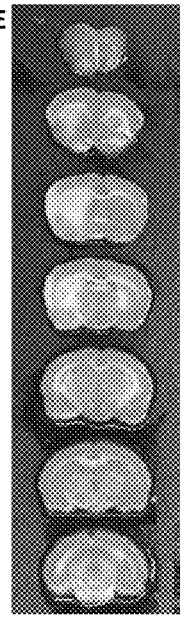
Figure 1G:
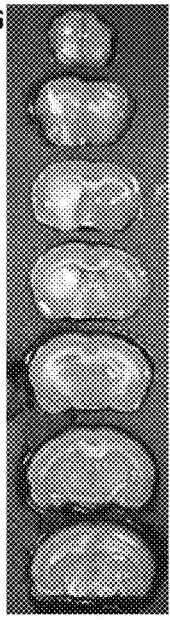
Figure 1B:
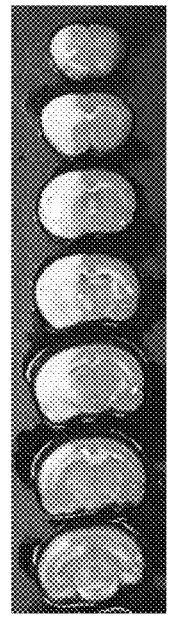
Figure 1D:
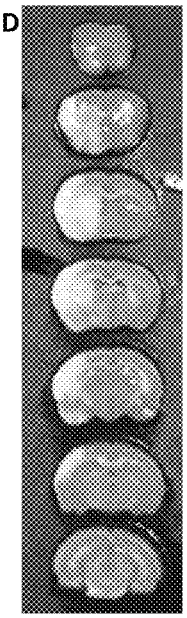
Figure 1F:
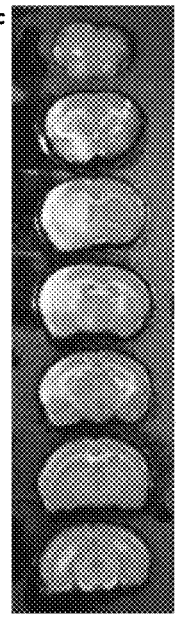
Figure 1H:
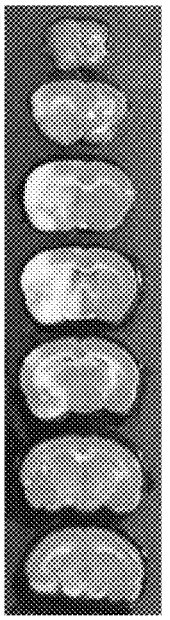

There is evidence that administration of anticoagulants and/or thrombolytic therapy, such as tissue plasminogen activator (tPA) can improve survival of patients with coronavirus-induced ARDS. However, thrombolytic therapies are often associated with adverse side effects such as hemorrhage and vascular instability. Compounds disclosed herein can protect a patient against the adverse effects of a thrombolytic or anticoagulant therapy. Accordingly, compounds disclosed herein can be used in combination with a thrombolytic therapy to treat and/or prevent a coronavirus infection and/or coronavirus-induced DIC and/or respiratory distress.

In some aspects, presented herein is a method of preventing, reducing a risk of, inhibiting, reducing, mitigating or treating a coronavirus infection, coronavirus-induced respiratory distress, coronavirus-induced disseminated intravascular coagulation (DIC) and/or coronavirus-induced vascular instability in a subject, comprising administering to the subject (i) a therapeutically effective amount of a thrombolytic therapy or an anticoagulant, and/or (ii) a therapeutically effective amount of a compound disclosed herein.

DETAILED DESCRIPTION

Compounds

In some embodiments provided herein is a compound for use in preventing or treating a coronavirus infection and/or coronavirus-induced DIC and/or coronavirus-induced respiratory distress. In some embodiments, a compound for use herein comprises the structure of Formula I;

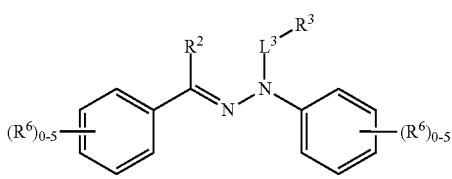

(I)

or a pharmaceutical acceptable salt, stereoisomer or tautomer thereof. In some embodiments of Formula I, $R^2$ is hydrogen (H) or methyl; $R^3$ is a methyl, a fluorine substituted alkyl (e.g., fluoromethyl, difluoromethyl, or trifluoromethyl), or a bromine substituted alkyl (e.g., bromomethyl, dibromomethyl, tribromomethyl); $L^3$ is a carbonyl; and $R^6$ at each occurrence is independently selected from alkyl, substituted alkyl, alkenyl, substituted alkenyl, cycloalkyl, substituted cycloalkyl, hydroxyl, methoxy, alkoxy, substituted alkoxy, aryloxy, substituted aryloxy, mercapto, alkylthio, arylthio, carbonyl, carboxyl, aryl, substituted aryl, substituted heterocyclic, halogen, cyano, cyanoalkyl, amine, methyl amine, dimethyl amine, nitro, amino, amidino, carbamate, $CF_3$, $OCF_3$, $S(O)_nR^7$, and $C(O)R^8$, or two $R^6$ at adjacent positions combine to form an optionally substituted heteroaryl or heteroalkyl ring fused with the adjoining phenyl moiety; where $R^7$ is selected from H, $R^9$, $NH_2$, $HNR^9$ and $NR^9R^{10}$; $R^8$ is selected from OH, $OR^9$, $NH_2$, $NHR^9$ and $NR^9R^{10}$; where $R^9$ and $R^{10}$ at each occurrence are independently an optionally substituted alkyl; and n is 1 or 2.

In certain embodiments of Formula I, $R^6$ at each occurrence is independently selected from alkyl, substituted alkyl, alkenyl, substituted alkenyl, hydroxyl, alkoxy, methoxy, substituted alkoxy, halogen, carbonyl, carboxyl, or $C(O)R^8$; and in certain such aspects, $R^6$ at each occurrence is methyl, methoxy, perfluoromethyl, perfluoromethoxy, hydroxyl, Cl, F, or I. In some embodiments of Formula I, $L^3$ is carbonyl, $R^3$ is $CF^3$, $R^2$ is H, and $R^6$ is null or H at every occurrence. In some embodiments of Formula I, $L^3$ is carbonyl, $R^3$ is $CF_3$, $R^2$ is H, and $R^6$ is independently selected from methyl or methoxy, at each occurrence. In some embodiments of Formula I, $L^3$ is carbonyl, $R^3$ is $CF_3$, $R^2$ is methyl, and $R^6$ is independently selected from methyl or methoxy, at each occurrence.

In some embodiments, a compound for use herein comprises the structure of Formula II;

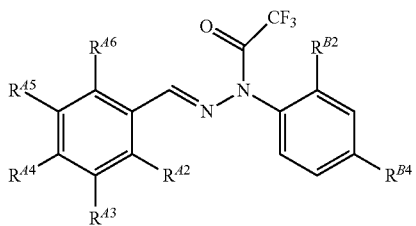

or a pharmaceutically acceptable salt, stereoisomer or tautomer thereof, where:
(i) $R^{A2}$, $R^{A4}$, $R^{A5}$, and $R^{A6}$ is H, $R^{A3}$ is methoxy, $R^{B2}$ is methyl, and $R^{B4}$ is methyl;
(ii) $R^{A2}$, $R^{A3}$, $R^{A5}$, and $R^{A6}$ is H, $R^{A4}$ is methoxy, $R^{B2}$ is methyl, and $R^{B4}$ is methyl;
(iii) $R^{A2}$, $R^{A3}$, $R^{A4}$, $R^{A5}$, and $R^{A6}$ is H, $R^{B2}$ is H, and $R^{B4}$ is H;
(iv) $R^{A2}$, $R^{A3}$, $R^{A4}$, $R^{A5}$, and $R^{A6}$ is H, $R^{B2}$ is methyl, and $R^{B4}$ is methyl;
(v) $R^{A2}$, $R^{A4}$, $R^{A5}$, and $R^{A6}$ is H, $R^{A3}$ is methoxy, $R^{B2}$ is H, and $R^{B4}$ is H;
(vi) $R^{A2}$, $R^{A3}$, $R^{A4}$, $R^{A5}$, and $R^{A6}$ is H, $R^{B2}$ is H, and $R^{B4}$ is methyl;
(vii) $R^{A2}$, $R^{A4}$, $R^{A5}$, and $R^{A6}$ is H, $R^{A3}$ is methoxy, $R^{B2}$ is H, and $R^{B4}$ is methyl;
(viii) $R^{A2}$, $R^{A3}$, $R^{A4}$, $R^{A5}$, and $R^{A6}$ is H, $R^{B2}$ is methyl, and $R^{B4}$ is H;
(ix) $R^{A2}$, $R^{A4}$, $R^{A5}$, and $R^{A6}$ is H, $R^{A3}$ is methoxy, $R^{B2}$ is methyl, and $R^{B4}$ is H;
(x) $R^{A2}$, $R^{A3}$, $R^{A5}$, and $R^{A6}$ is H, $R^{A4}$ is COOH, $R^{B2}$ is methyl, and $R^{B4}$ is methyl;
(xi) $R^{A2}$, $R^{A4}$, and $R^{A5}$ is H, $R^{A3}$ and $R^{A6}$ is hydroxyl, $R^{B2}$ is methyl, and $R^{B4}$ is methyl;
(xii) $R^{A2}$, $R^{A4}$, and $R^{A6}$ is H, $R^{A3}$ and $R^{A5}$ is hydroxyl, $R^{B2}$ is methyl, and $R^{B4}$ is methyl;
(xiii) $R^{A2}$, $R^{A4}$, and $R^{A5}$ is H, $R^{A3}$ is methoxy, $R^{A6}$ is F, $R^{B2}$ is H, and $R^{B4}$ is Cl;
(xiv) $R^{A3}$ and $R^{A5}$ is H, $R^{A2}$ and $R^{A6}$ is F, $R^{A4}$ is hydroxyl, $R^{A6}$ is F, $R^{B2}$ is H, and $R^{B4}$ is F;
(xv) $R^{A2}$, $R^{A4}$, and $R^{A6}$ is H, $R^{A3}$ is hydroxyl, $R^{A5}$ is F, $R^{B2}$ is H, and $R^{B4}$ is F; or
(xvi) $R^{A2}$, $R^{A5}$, and $R^{A6}$ is H, $R^{A3}$ and $R^{A4}$ taken together are —O—$CH_2$—O—, $R^{A5}$ is F, $R^{B2}$ is H, and $R^{B4}$ is F.

In some embodiments of the compound of Formula II, $R^{A2}$, $R^{A5}$, and $R^{A6}$ are H, $R^{A3}$ is methoxy, $R^{B2}$ and $R^{B4}$ are methyl, and $R^{A4}$ is selected from H, $NO_2$, OH, methoxy, phenol, methyl, Fluorine (F), $N(CH_3)_2$, $CHC(CN)_2$ and O-tert-butyldimethylsilyl (OTBDMS). In some embodiments of the compound of Formula II, $R^{A2}$, $R^{A4}$, $R^{A5}$, and $R^{A6}$ are H, $R^{A3}$ is methoxy, $R^{B2}$ is methyl, and $R^{B4}$ is methyl. In some embodiments of the compound of Formula II, $R^{A2}$, $R^{A3}$, $R^{A5}$, and $R^{A6}$ are H, $R^{A4}$ is methoxy, $R^{B2}$ is methyl, and $R^{B4}$ is methyl. In some embodiments of the compound of Formula II, $R^{A2}$, $R^{A3}$, $R^{A4}$, $R^{A5}$ and $R^{A6}$ are H, $R^{B2}$ is methyl, and $R^{B4}$ is methyl. In some embodiments of the compound of Formula II, $R^{A2}$, $R^{A4}$, $R^{A5}$ and $R^{A6}$ are H, $R^{A3}$ is methoxy, $R^{B2}$ is H, and $R^{B4}$ is H. In some embodiments of the compound of Formula II, $R^{A2}$, $R^{A3}$, $R^{A4}$, $R^{A5}$ and $R^{A6}$ are H, $R^{B2}$ is H, and $R^{B4}$ is methyl. In some embodiments of the compound of Formula II, $R^{A2}$, $R^{A3}$, $R^{A4}$, $R^{A5}$ and $R^{A6}$ are H, $R^{B2}$ is H, and $R^{B4}$ is methyl. In some embodiments of the compound of Formula II, $R^{A2}$, $R^{A4}$, $R^{A5}$ and $R^{A6}$ are H, $R^{A3}$ is methoxy, $R^{B2}$ is H, and $R^{B4}$ is methyl. In some embodiments of the compound of Formula II, $R^{A2}$, $R^{A4}$, $R^{A5}$ and $R^{A6}$ are H, $R^{A3}$ is methoxy, $R^{B2}$ is methyl, and $R^{B4}$ is H. In some embodiments of the compound of Formula II, $R^{A2}$, $R^{A3}$, $R^{A4}$, $R^{A5}$ and $R^{A6}$ are H, $R^{B2}$ is methyl, and $R^{B4}$ is H. In some embodiments of the compound of Formula II, $R^{A2}$, $R^{A3}$, $R^{A5}$ and $R^{A6}$ are H, $R^{A4}$ is a carboxyl, $R^{B2}$ is methyl, and $R^{B4}$ is methyl. In some embodiments of the compound of Formula II, $R^{A2}$, $R^{A4}$, $R^{A5}$ and $R^{A6}$ are H, $R^{A3}$ is a carboxyl, $R^{B2}$ is methyl, and $R^{B4}$ is methyl.

In some embodiments, a compound for use herein comprises the structure of Formula III;

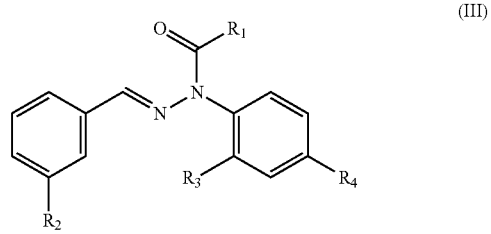

(III)

or a pharmaceutically acceptable salt, stereoisomer or tautomer thereof, where $R_1$ is methyl, fluoromethyl, difluoromethyl, trifluoromethyl, bromomethyl, dibromomethyl or tribromomethyl; $R_2$ is methyl, methoxy, hydroxyl, halogen, $CF_3$, $OCH_3$, $OCF_3$ or $OCBr_3$; and $R_3$ and $R_4$ are independently selected from hydrogen, hydroxyl, a halogen (e.g., Cl, F or Br), methyl, a methoxy, and an amine. In some embodiments of Formula III, $R_1$ is $CF_3$ (trifluoromethyl), $R_2$ is $OCH_3$, and $R_3$ and $R_4$ are methyl. In some embodiments of Formula III, $R_1$ is $CF_3$ (trifluoromethyl), $R_2$ is $OCF_3$, and $R_3$ and $R_4$ are methyl In some embodiments, a compound for use herein comprises the structure of Formula IV below, or a pharmaceutically acceptable salt, stereoisomer or tautomer thereof.

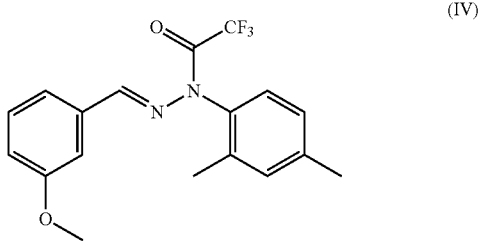 [SMILES: COc1cccc(/C=N/N(C(=O)C(F)(F)F)c2ccc(C)cc2C)c1]

(IV)

The structure of Formula IV is sometimes referred to herein as "J147".

The following terms have the respective definitions set out below.

"Alkyl" refers to straight or branched chain alkyl radicals having in the range of about 1 up to about 12 carbon atoms (e.g., methyl, ethyl, propyl, butyl, and the like). "Substituted alkyl" refers to alkyl further bearing one or more substituents (e.g., 1, 2, 3, 4, or even 5) as set forth herein. "Optionally substituted alkyl" refers to alkyl or substituted alkyl.

"Cycloalkyl" refers to cyclic ring-containing groups containing in the range of about 3 up to about 12 carbon atoms. "Substituted cycloalkyl" refers to cycloalkyl further bearing one or more substituents (e.g., 1, 2, 3, 4, or even 5) selected from alkyl, substituted alkyl, as well as any of the substituents set forth herein. "Optionally substituted cycloalkyl" refers to cycloalkyl or substituted cycloalkyl.

"Heterocycle," "heterocyclic" and like terms refer to cyclic (i.e., ring-containing) groups containing one or more heteroatoms (e.g., N, O, S, or the like) as part of the ring, and having in the range of 1 up to about 14 carbon atoms. "Substituted heterocyclic" and like terms refer to heterocycle further bearing one or more substituents (e.g., 1, 2, 3, 4, or even 5) as set forth herein. Exemplary heterocyclic moieties include saturated rings, unsaturated rings, and aromatic heteroatom-containing ring systems, e.g., epoxy, tetrahydrofuran, oxazoline, pyrrole, pyridine, furan, and the like. "Optionally substituted heterocycle" and like terms refer to heterocycle or substituted heterocycle.

Reference to "optionally substituted bicyclic ring" refers to a bicyclic ring structure as known in the art, optionally including substitutions as defined herein.

"Alkenyl" refers to straight, branched chain, or cyclic hydrocarbyl groups including from 2 to about 20 carbon atoms having at least one, 1-3, 1-2, or one, carbon to carbon double bond. "Substituted alkenyl" refers to alkenyl substituted at 1 or more, e.g., 1, 2, 3, 4, or even 5 positions, with substitution as described herein. "Optionally substituted alkenyl" refers to alkenyl or substituted alkenyl. In some embodiments, an alkenyl is ethylenyl or propylenyl. In certain embodiments, a substituted alkenyl is a substituted ethylenyl or substituted propylenyl. In some embodiments, ethylenyl or propylenyl is substituted with one or more CN moieties. For example, in some embodiments, a substituted ethylenyl comprises $(CN)_2C=CH-$.

"Aryl" refers to aromatic groups having in the range of 6 up to about 14 carbon atoms. "Substituted aryl" refers to aryl radicals further bearing one or more substituents (e.g., 1, 2, 3, 4, or even 5) selected from alkyl, substituted alkyl, cycloalkyl, substituted cycloalkyl, hydroxyl, alkoxy, aryloxy, mercapto, alkylthio, arylthio, carbonyl, aryl, substituted aryl, heterocyclic, substituted heterocyclic, halogen, trifluoromethyl, pentafluoroethyl, cyano, cyanoalkyl, nitro, amino, amido, amidino, carboxyl, carbamate, $SO_2X$, wherein X is H, R, $NH_2$, NHR or $NR_2$, $SO_3Y$, wherein Y is H, $NH_2$, NHR or $NR_2$, or C(O)Z, wherein Z is OH, OR, $NH_2$, NHR or $NR_2$, and the like. "Optionally substituted aryl" refers to aryl or substituted aryl.

"Aralkyl" refers to an alkyl group substituted by an aryl group. "Substituted aralkyl" refers to aralkyl further bearing one or more substituents (e.g., 1, 2, 3, 4, or even 5) selected from alkyl, substituted alkyl, cycloalkyl, substituted cycloalkyl, as well as any of the substituents set forth herein. Thus, aralkyl groups include benzyl, diphenylmethyl, and 1-phenylethyl ($-CH(C_6H_5)(CH_3)$) among others. "Optionally substituted aralkyl" refers to aralkyl or substituted aralkyl.

"Heteroaryl" refers to aromatic groups containing one or more heteroatoms (e.g., N, O, S, or the like) as part of the aromatic ring, typically having in the range of 2 up to about 14 carbon atoms, and "substituted heteroaryl" refers to heteroaryl radicals further bearing one or more substituents (e.g., 1, 2, 3, 4, or even 5) selected from alkyl, substituted alkyl, cycloalkyl, substituted cycloalkyl, as well as any of the substituents set forth above.

"Heteroaralkyl" and "heteroarylalkyl" refer to an alkyl group substituted by one or more heteroaryl groups. "Substituted heteroaralkyl" refers to heteroaralkyl further bearing one or more substituents (e.g., 1, 2, 3, 4, or even 5) selected from alkyl, substituted alkyl, cycloalkyl, substituted cycloalkyl, as well as any of the substituents set forth herein. "Optionally substituted heteroaralkyl" refers to heteroaralkyl or substituted heteroaralkyl.

"Halogen" and "halo" refer to fluorine, chlorine, bromine or iodine.

"Hydroxyl" and "hydroxy" refer to the functionality —OH.

"Alkoxy" denotes the group —OR, where R is alkyl. "Substituted alkoxy" denotes the group —OR, where R is substituted alkyl. "Optionally substituted alkoxy" refers to alkoxy or substituted alkoxy.

"Aryloxy" denotes the group —OR, where R is aryl. "Substituted aryloxy" denotes the group —OR, where R is substituted aryl. "Optionally substituted aryloxy" refers to aryloxy or substituted aryloxy.

"Mercapto" and "thiol" refer to the functionality —SH.

"Alkylthio" and "thioalkoxy" refer to the group —SR, $-S(O)_{n=1-2}-R$, where R is alkyl. "Substituted alkylthio" and "substituted thioalkoxy" refers to the group —SR, $-S(O)_{n=1-2}-R$, where R is substituted alkyl. "Optionally substituted alkylthio" and "optionally substituted thioalkoxy" refers to alkylthio or substituted alkylthio.

"Arylthio" denotes the group —SR, where R is aryl. "Substituted arylthio" denotes the group —SR, where R is substituted aryl. "Optionally substituted arylthio" refers to arylthio or substituted arylthio.

"Amino" refers to unsubstituted, monosubstituted and disubstituted amino groups, including the substituent —NH$_2$, "monoalkylamino," which refers to a substituent having structure —NHR, wherein R is alkyl or substituted alkyl, and "dialkylamino," which refers to a substituent of the structure —NR$_2$, wherein each R is independently alkyl or substituted alkyl.

"Amidino" denotes the group —C(=NR$^q$)NR'R$^s$, wherein R$^q$, R$^r$, and R$^s$ are independently hydrogen or optionally substituted alkyl.

Reference to "amide group" embraces substituents of the structure C(O)—NR$_2$, wherein each R is independently H, alkyl, substituted alkyl, aryl or substituted aryl as set forth above. When each R is H, the substituent is also referred to as "carbamoyl" (i.e., a substituent having the structure —C(O)—NH$_2$). When only one of the R groups is H, the substituent is also referred to as "monoalkylcarbamoyl" (i.e., a substituent having the structure —C(O)—NHR, wherein R is alkyl or substituted alkyl as set forth above) or "arylcarbamoyl" (i.e., a substituent having the structure —C(O)—NH(aryl), wherein aryl is as defined above, including substituted aryl). When neither of the R groups are H, the substituent is also referred to as "di-alkylcarbamoyl" (i.e., a substituent having the structure —C(O)—NR$_2$, wherein each R is independently alkyl or substituted alkyl as set forth above).

Reference to "carbamate" embraces substituents of the structure —O—C(O)—NR$_2$, wherein each R is independently H, alkyl, substituted alkyl, aryl or substituted aryl.

Reference to "ester group" embraces substituents of the structure —O—C(O)—OR, wherein each R is independently alkyl, substituted alkyl, aryl or substituted aryl.

"Acyl" refers to groups having the structure —C(O)R, where R is hydrogen, alkyl, aryl, and the like as defined herein. "Substituted acyl" refers to acyl wherein the substituent R is substituted as defined herein. "Optionally substituted acyl" refers to acyl and substituted acyl.

"Cyanoalkyl" refers to the group —R≡N, wherein R is an optionally substituted alkylenyl.

As used here, "substitution" denotes an atom or group of atoms that has been replaced with another atom or group of atoms (i.e., substituent), and includes all levels of substitution, e.g. mono-, di-, tri-, tetra-, penta-, or even hex-substitution, where such substitution is chemically permissible. Substitutions can occur at any chemically accessible position and on any atom, such as substitution(s) on carbon and any heteroatom, such as oxygen, nitrogen, or sulfur. For example, substituted moieties include those where one or more bonds to a hydrogen or carbon atom(s) contained therein are replaced by a bond to non-hydrogen and/or non-carbon atom(s). Substitutions can include, but are not limited to, a halogen atom such as F, Cl, Br, and I; an oxygen atom in groups such as hydroxyl groups, alkoxy groups, aryloxy groups, and ester groups; a sulfur atom in groups such as thiol groups, alkyl and aryl sulfide groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and heteroatoms in other groups as well known in the art.

Non-limiting examples of substituents include, without limitation, halogen, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR, —SR, —OC(O)R, —OC(S)R, —C(O)R, —C(S)R, —C(O)OR, —C(S)OR, —S(O)R, —S(O)$_2$R, —C(O)NHR, —C(S)NHR, —C(O)NRR, —C(S)NRR, —S(O)$_2$NHR, —S(O)$_2$NRR, —C(NR)NHR, —C(NH)NRR, —NHC(O)R, —NHC(S)R, —NRC(O)R, —NRC(S)R, —NHS(O)$_2$R, —NRS(O)$_2$R, —NHC(O)NHR, —NHC(S)NHR, —NRC(O)NH$_2$, —NRC(S)NH$_2$, —NRC(O)NHR, —NRC(S)NHR, —NHC(O)NRR, —NHC(S)NRR, —NRC(O)NRR, —NRC(S)NRR, —NHS(O)$_2$NHR, —NRS(O)$_2$NH$_2$, —NRS(O)$_2$NHR, —NHS(O)$_2$NRR, —NRS(O)$_2$NRR, —NHR, —NRR, where R at each occurrence is independently H, optionally substituted alkyl, optionally substituted aryl, or optionally substituted heteroaryl. Also contemplated is substitution with an optionally substituted hydrocarbyl moiety containing one or more of the following chemical functionalities: —O—, —S—, —NR—, —O—C(O)—, —O—C(O)—O—, —O—C(O)—NR—, —NR—C(O)—, —NR—C(O)—O—, —NR—C(O)—NR—, —S—C(O)—, —S—C(O)—O—, —S—C(O)—NR—, —S(O)—, —S(O)$_2$—, —O—S(O)$_2$—, —O—S(O)$_2$—O, —O—S(O)$_2$—NR—, —O—S(O)—, —O—S(O)—O—, —O—S(O)—NR—, —O—NR—C(O)—, —O—NR—C(O)—O—, —O—NR—C(O)—NR—, —NR—O—C(O)—, —NR—O—C(O)—O—, —NR—O—C(O)—NR—, —O—NR—C(S)—, —O—NR—C(S)—O—, —O—NR—C(S)—NR—, —NR—O—C(S)—, —NR—O—C(S)—O—, —NR—O—C(S)—NR—, —O—C(S)—, —O—C(S)—O—, —O—C(S)—NR—, —NR—C(S)—, —NR—C(S)—O—, —NR—C(S)—NR—, —S—S(O)$_2$—, —S—S(O)$_2$—O—, —S—S(O)$_2$—NR—, —NR—O—S(O)—, —NR—O—S(O)—O—, —NR—O—S(O)—NR—, —NR—O—S(O)$_2$—, —NR—O—S(O)$_2$—NR—, —O—NR—S(O)—, —O—NR—S(O)—O—, —O—NR—S(O)—NR—, —O—NR—S(O)$_2$—O—, —O—NR—S(O)$_2$—NR—, —O—NR—S(O)$_2$—, —O—P(O)R$_2$—, —S—P(O)R$_2$—, or —NRP(O)R$_2$—, where R at each occurrence is independently H, optionally substituted alkyl, optionally substituted aryl, or optionally substituted heteroaryl.

In some embodiments, a compound for use herein includes isomers including stereoisomers (e.g., enantiomer and diastereomers), constitutional isomers, tautomers, conformational isomers, and geometric isomers of a compound disclosed herein.

Exemplary constitutional isomers include for example without limitation, isomers resulting from different connectivity of functionalities forming the compounds disclosed herein, for example, 1-propyl versus 2-propyl substitution, and the like. Constitutional isomers in combination with tautomerization additionally embrace bonding rearrangements involving the migration of double bonds and substituents. For example, tautomerization in combination with a 1-3 pleiotropic hydrogen shift can result in constitutional isomerism.

Exemplary conformational isomers include for example without limitation, isomers produced by rotation about a bond wherein the rotation is hindered to the extent that separable isomers result, as well known in the art.

Exemplary geometrical isomers include double bonds in e.g., the "E" or "Z" configuration, as well known in the art.

Compounds disclosed herein can be readily prepared using a suitable synthetic method.

For example, 3-methoxy benzaldehyde can be condensed with 2,4-dimethylphenyl hydrazine in methanol employing standard hydrazone preparation conditions (e.g., heating in the microwave to speed the reaction time). Next, the free NH is acylated with TFAA (trifluoroacetic anhydride) plus catalytic (0.1%) amounts of DMAP (dimethylamino pyridine), THF (tetrahydrofuran) or DCM (dichloromethane).

In some embodiments, a compound for use herein is provided in the form of pharmaceutically acceptable salt. A compound for use herein can be complexed with any suitable inorganic or organic salt using a suitable method. In some embodiments, a salt of a compound for use herein is prepared by reacting the compound with a suitable organic or inorganic acid or base. Non-limiting examples of organic salts contemplated for use herein include methanesulfonate, acetate, oxalate, adipate, alginate, aspartate, valerate, oleate, laurate, borate, benzoate, lactate, phosphate, toluenesulfonate (tosylate), citrate, malate, maleate, fumarate, succinate, tartrate, napsylate, methanesulfonate, 2-naphthalenesulfonate, nicotinate, benzenesulfonate, butyrate, camphorate, camphorsulfonate, cyclopentanepropionate, digluconate, dodecylsulfate, glucoheptanoate, glycerophosphate, heptanoate, hexanoate, undecanoate, 2-hydroxyethanesulfonate, ethane sulfonate, and the like. In some embodiments, inorganic salts can be formed from inorganic acids such as sulfate, bisulfate, hemisulfate, hydrochloride, chlorate, perchlorate, hydrobromide, hydroiodide, and the like. Non-limiting examples of a base salt include ammonium salts; alkali metal salts such as sodium salts, potassium salts, and the like; alkaline earth metal salts such as calcium salts, magnesium salts, and the like; salts with organic bases such as dicyclohexylamine salts, N-methyl-D-glucamine, phenylethylamine, and the like; and salts with amino acids such as arginine, lysine, and the like.

In some embodiments, compounds disclosed herein are useful for treating a subject having a coronavirus infection when used in combination with a thrombolytic therapy or anti-coagulant. Accordingly, in certain embodiments, a method herein comprises, in part, administering a therapeutically effect amount of a compound of Formula I, II, III or IV to a subject.

Coagulation, Respiratory Distress & Coronavirus

Disseminated intravascular coagulation (DIC) is a condition in which blood clots form throughout the body, blocking small blood vessels. Symptoms may include chest pain, shortness of breath, leg pain, problems speaking, or problems moving parts of the body. As clotting factors and platelets are used up, bleeding may occur. This may include blood in the urine, blood in the stool, or bleeding into the skin. Complications may include respiratory distress and organ failure.

A coronavirus infection can cause severe DIC (coronavirus-induced DIC) which is often evidenced by high venous thromboembolism rates, elevated D-dimer levels, high fibrinogen levels, low antithrombin levels, and/or pulmonary congestion with microvascular thrombosis and occlusion. In some embodiments, a coronavirus infection is also associated with severe respiratory distress thought to be caused in part, by fibrin deposition in the pulmonary microvasculature. Respiratory distress refers to a potentially life-threatening condition associated with fluid build-up in the lungs (pulmonary edema) that results in an inability to maintain adequate blood oxygen levels (hypoxia or hypoxemia). Non-limiting examples of respiratory distress include acute respiratory distress, acute respiratory distress syndrome (ARDS), and severe acute respiratory syndrome (SARS). Severe ARDS with concomitant diagnosis of DIC is observed in greater than 70% of those who die of COVID-19.

Coronavirus-induced DIC can be treated and/or mitigated by administration of a thrombolytic therapy and/or by administration of an anti-coagulant. In some embodiments, a coronavirus patient may be treated with anticoagulants such as tPA, unfractionated heparin, low-molecular-weight heparins, direct oral anticoagulants (DOACs), aspirin, clopidogrel, prasugrel or ticagrelor. In some embodiments, a coronavirus patient, with or without presentation of respiratory distress, can be treated by administration of tPA.

However, thrombolytic therapy can cause a number of adverse effects. Many thrombolytic therapies, such as tPA, can induce hemorrhage and vascular instability.

In some embodiments, vascular instability comprises endothelial dysfunction, non-limiting examples of which include a reduction or loss of vascular tone, a reduction or loss of hemostasis, edema (e.g., localized swelling), damage and/or dysfunction of the vascular endothelium, damage or disruption of the blood brain barrier, the like and combinations thereof. In some embodiments, vascular instability comprises edema. In some embodiments, edema is cerebral edema. In some embodiments, edema comprises swelling of the blood brain barrier.

In some embodiments, vascular instability comprises reperfusion injury. Reperfusion injury often results from reperfusion of blood to a tissue that was deprived of blood flow due to a blood clot or thrombosis. Administration of a thrombolytic therapy or anticoagulant can dissolve blood clots resulting in reperfusion injury. Reperfusion injury often includes damage to, or injury of, the vascular endothelium due to reperfusion (e.g., reperfusion induced by a thrombolytic therapy or an anticoagulant; e.g., reperfusion injury).

The compounds presented herein can prevent, reduce a risk of, inhibit, reduce, mitigate, and/or treat vascular instability induced by a thrombolytic therapy or an anticoagulant. Compounds disclosed herein can stabilize vascular endothelium and/or stabilize a blood brain barrier during or after reperfusion, and/or during or after administration of a thrombolytic therapy or an anticoagulant. Compounds disclosed herein can also allow for a more aggressive dosing regimen of a thrombolytic therapy (e.g., tPA treatment).

Accordingly, in some embodiments, methods presented herein comprise administration of a compound disclosed herein in combination with a thrombolytic therapy or an anticoagulant for the treatment of a coronavirus infection. In some embodiments, methods presented herein include administration of a compound disclosed herein in combination with a thrombolytic therapy or an anticoagulant for the treatment of coronavirus-induced DIC and/or for coronavirus-induced respiratory distress. Compounds disclosed herein can be administered prior to, with or after a thrombolytic therapy or anticoagulant.

In some cases a coronavirus infection can induce hemorrhage and/or coagulopathy thought to be due to depletion of platelets and an increase in endogenous plasma levels of tPA. In some embodiments, subjects that experience coronavirus induced hemorrhage display elevated endogenous tPA levels and/or elevated plasminogen activator inhibitor-1 (PAI-1) levels in their blood or plasma (Zuo, Yu et al. (Dec. 5, 2020) *Plasma tissue plasminogen activator and plasminogen activator inhibitor-1 in hospitalized COVID-19 patients*, medRxiv preprint doi: https://doi.org/10.1101/2020.08.29.20184358).

High endogenous levels of tPA and/or PAI-1 can result in vascular instability similar that observed upon administration of tPA. Therefore, in certain embodiments, methods presented herein comprise administration of a compound disclosed herein for the treatment of a coronavirus infection. In some embodiments, methods presented herein include administration of a compound disclosed herein for the prevention or treatment of coronavirus-induced respiratory distress. In some embodiments, methods presented herein include administration of a compound disclosed herein for the prevention or treatment of coronavirus-induced vascular instability.

Thrombolytic Therapies and Anti-Coagulants

A thrombolytic therapy often comprises administration of a suitable thrombolytic drug or thrombolytic agent to a subject to break up or dissolve a blood clot. Non-limiting examples of a thrombolytic drug or agent include a tissue plasminogen activator (tPA), a streptokinase, a streptokinase activator or a urokinase to a subject. Thrombolytic drugs or agents may comprise a recombinantly expressed protein. Non-limiting examples of a tPA include alteplase (Activase), reteplase (Retavase), or tenecteplase (TNKase, Metalyse). In some embodiments, a streptokinase activator is an anisoylated plasminogen streptokinase activator complex. Non-limiting examples of an anisoylated plasminogen streptokinase activator complex include anistreplase or eminase. In some embodiments, a urokinase is a urokinase-type plasminogen activator. An example of a urokinase-type plasminogen activator is saruplase.

In certain embodiments, a method comprises administering a compound disclosed herein to a subject before, during or after a subject is administered an anticoagulant. In certain embodiments, a method comprises administering a composition comprising a compound disclosed herein and an anticoagulant to a subject. An anticoagulant is often a drug or agent that is administered to a subject to inhibit or prevent blood clot formation. Non-limiting examples of an anticoagulant include vitamin K antagonist, a thrombin inhibitor, a Factor Xa inhibitor, heparin, a low molecular weight heparin, derivatives thereof, and the like. Non-limiting examples of a vitamin K antagonist include warfarin, acenocoumarol, coumatetralyl, dicoumarol, ethyl biscoumacetate, phenprocoumon, atromentin, clorindione, diphenadione, phenindione and tioclomarol. Non-limiting examples of a thrombin inhibitors include hirudins, bivalirudin, argatroban, dabigatran, Efegatran, inogatran, melagatran, ximelagatran, desirudin, lepirudin and antithrombin III. Non-limiting examples of a Factor Xa inhibitor include low molecular weight heparins (e.g., bemiparin, certoparin, dalteparin, enoxaparin, nadroparin, pamaparin, reviparin, and tinzaparin), apixaban (Eliquis), betrixaban, darexaban, otamixaban, fondaparinux, rivaroxaban (Xarelto), edoxaban (Lixiana), etmixaan, fondaparinux, idraparinux, and heparinoids (e.g., danaparioid, dermatan sulfate and sulodexide). Non-limiting examples of heparin, low molecular weight heparins and heparin derivatives include enoxaparin, dalteparin, tinzaparin and danaparoid. Other non-limiting examples of anti-coagulants include dabigatran (Pradaxa), batroxobin, hementin, clopidogrel, ticlopidine, prasugrel, ticagrelor, and aspirin.

In certain embodiments, a hemorrhage or vascular instability is induced by, caused by (directly or indirectly), worsened by, aggravated by, exacerbated by, and/or magnified by an antiplatelet drug, non-limiting examples of which include a glycoprotein IIb/IIIa inhibitor (e.g., abciximab, eptifibatide, orbofiban, roxifiban, sibrafiban and tirofiban), an ADP receptor/P2Y$_{12}$ inhibitor (e.g., thienopyridines (e.g., clopidogrel, prasugrel and ticlopidine) and nucleotide/nucleoside analogs (e.g., cangrelor, elinogrel and ticagrelor)), a prostaglandin analogue (PGI2)(e.g., beraprost, iloprost, prostacyclin and treprostinil), a cyclooxygenase (COX) inhibitor (e.g., acetylsalicylic acid/aspirin, aloxiprin, carbasalate calcium, indobufen and triflusal), a thromboxane inhibitor (e.g., thromboxane synthase inhibitors (e.g., dipyridamole, picotamide and terbogrel), receptor antagonists (e.g., terbogrel and terutroban)), cloricromen, ditazole and vorapaxar.

Coronavirus Infection of the Central Nervous System

A coronavirus infection may involve neuronal infection within the central nervous system ("CNS"). Coronavirus neuroinvasion may cause locally hypoxic regions in the CNS and disturbance of vasculature in the CNS, and the disruption of brain vasculature can make vulnerable ischemic infarcts and regions more susceptible to viral invasion. See Song, Eric et al., "Neuroinvasion of SARS-CoV-2 in human and mouse brain," bioRxiv preprint doi: https://doi.org/10.1101/2020.06.25.169946 (Sep. 8, 2020) which is incorporated herein by reference in its entirety. In certain embodiments, a subject suffering from a coronavirus infection is administered a compound of the invention for the purpose of reducing a risk of, inhibiting, reducing, mitigating or treating a coronavirus infection of the central nervous system, coronavirus-induced pathology of central nervous system neurons, local hypoxia in the central nervous system, and/or coronavirus-induced vascular instability in the central nervous system. In certain such embodiments the compound of the invention is J147. In certain embodiments the subject is additionally treated with a therapeutically effective amount of a thrombolytic therapy or an anticoagulant. In certain such embodiments the thrombolytic therapy comprises administering a therapeutically effective amount of tPA, unfractionated heparin, low-molecular-weight heparins, direct oral anticoagulants (DOACs), aspirin, clopidogrel, prasugrel or ticagrelor in a subject. In certain embodiments, the thrombolytic therapy comprises administration of a therapeutically effective amount of unfractionated heparin, low-molecular-weight heparins, or direct oral anticoagulants (DOACs). In certain embodiments, the thrombolytic therapy comprises administration of a therapeutically effective amount of tPA.

Coronavirus Infection

A coronavirus refers to a human pathogenic virus of the family Coronaviridae. In some embodiments, a coronavirus is a human pathogenic virus of the subfamily Orthocoronavirinae. In some embodiments, a coronavirus is a virus of the genus Alphacoronavirus or Betacoronavirus. In certain embodiments, a coronavirus is selected from Human coronavirus 229E, Human coronavirus NL63, Betacoronavirus 1 (Human coronavirus OC43), Human coronavirus HKU1, Middle East respiratory syndrome-related coronavirus, and severe acute respiratory syndrome-related coronavirus (e.g., SARS-CoV, and SARS-CoV-2). In certain embodiments, a coronavirus is severe acute respiratory syndrome (SARS) coronavirus (SARS-CoV), SARS-coronavirus-2 (SARS-CoV-2, or a natural variant or strain thereof. In some embodiments, a coronavirus infection caused by SARS-CoV-2 is referred to a COVID-19.

Subjects

The term "subject" refers to a mammal. Any suitable mammal can be treated by a method or composition described herein. Non-limiting examples of mammals include a human, non-human primate (e.g., ape, gibbons, chimpanzees, orangutans, monkeys, macaques, and the like), domestic animals (e.g., dogs and cats), farm animals (e.g., horses, cows, goats, sheep, pigs) and experimental animals (e.g., mouse, rat, rabbit, guinea pig). In some embodiments a subject is a non-human primate or a human. In some embodiments a subject is a human. A subject can be any age or at any stage of development (e.g., an adult, teen, child, infant, or a mammal in utero). In some embodiments, a subject is over the age of 50 years of age, or over the age of 60 years of age. A subject can be male or female.

In certain embodiments, a subject is scheduled to receive or is about to receive a thrombolytic, anti-coagulant or endovascular intervention therapy. In certain embodiments, a subject is administered a thrombolytic, anti-coagulant or endovascular intervention therapy. In certain embodiments, a subject is administered tPA.

In some embodiments, a subject is infected with a coronavirus. In certain embodiments, a subject is infected with SARS-CoV, SARS-CoV-2, or a natural variant or strain thereof. In some embodiments, a subject has COVID-19.

In some embodiments, a subject has respiratory distress. In some embodiments, the respiratory distress is induced by a coronavirus infection. In certain embodiments, a subject has, or is suspected of having a coronavirus-induced respiratory distress. In some embodiments, a subject has respiratory distress induced by SARS-CoV, SARS-a SARS-CoV-2, or a natural variant or strain thereof. In some embodiments, a subject has respiratory distress induced by COVID-19. In some embodiments, a subject has a respiratory distress (e.g., coronavirus-induced respiratory distress) selected from an acute respiratory distress, acute respiratory distress syndrome (ARDS), and severe acute respiratory syndrome (SARS).

In certain embodiments, a subject is at risk of being intubated, and/or at risk of being operably connected to a ventilator. In certain embodiments, a subject is intubated, and/or is operably connected to a ventilator.

In some embodiments a subject has a coronavirus-induced respiratory distress and a high blood or plasma level of endogenous tPA and/or plasminogen activator inhibitor-1 (PAI-1). In certain embodiments, a subject has an average, mean or absolute blood or plasma level of endogenous tPA above 30 ng/ml (wt/vol.), above 40 ng/ml, above 50 ng/ml, above 60 ng/ml, above 70 ng/ml, above 80 ng/ml, above 90 ng/ml, or above 100 ng/ml. In certain embodiments, a subject has an average, mean or absolute blood or plasma level of endogenous tPA in a range of 30 ng/ml to 500 ng/ml, 40 ng/ml to 500 ng/ml, 50 ng/ml to 500 ng/ml, 60 ng/ml to 500 ng/ml, 70 ng/ml to 500 ng/ml, 80 ng/ml to 500 ng/ml, 90 ng/ml to 500 ng/ml, 100 ng/ml to 500 ng/ml.

In certain embodiments, a subject has an average, mean or absolute blood or plasma level of PAI-1 above 30 ng/ml (wt/vol.), above 40 ng/ml, above 50 ng/ml, above 60 ng/ml, above 70 ng/ml, above 80 ng/ml, above 90 ng/ml, or above 100 ng/ml. In certain embodiments, a subject has an average, mean or absolute blood or plasma level of PAI-1 in a range of 30 ng/ml to 500 ng/ml, 40 ng/ml to 500 ng/ml, 50 ng/ml to 500 ng/ml, 60 ng/ml to 500 ng/ml, 70 ng/ml to 500 ng/ml, 80 ng/ml to 500 ng/ml, 90 ng/ml to 500 ng/ml, 100 ng/ml to 500 ng/ml.

Hemorrhage

Some subjects infected with coronavirus experience severe hemorrhage that is induced directly or indirectly by the coronavirus, or induced by administration of a thrombolytic therapy or anticoagulant. In some embodiments, hemorrhage is an internal hemorrhage (e.g., internal bleeding), for example where the hemorrhage is not visible and/or is located and/or contained inside the body of the subject. Non-limiting examples of internal hemorrhage include internal bleeding into the chest, abdomen, neck, retroperitoneal space, pelvis, uterus, liver, heart, limbs, head, brain, tissues thereof and the like.

In some embodiments, coronavirus infected subjects may experience viral induced hemorrhage. In some embodiments, hemorrhage is induced by a thrombolytic therapy or an anticoagulant. In certain embodiments, a hemorrhage that is induced by a thrombolytic therapy or an anticoagulant is a hemorrhage that is caused by (directly or indirectly), worsened by, aggravated by, exacerbated by, and/or magnified by a thrombolytic therapy or by administration of an anticoagulant. Compounds disclosed herein can prevent, inhibit, mitigate, reduce the extent of, or delay the onset of hemorrhage that is caused by (directly or indirectly), worsened by, aggravated by, exacerbated by, and/or magnified by a coronavirus-infection, a thrombolytic therapy or administration of an anticoagulant. In certain embodiments, a hemorrhage that is induced by a thrombolytic therapy or an anticoagulant is a hemorrhage that is observed, diagnosed, or suspected to be present during or after administration of a thrombolytic therapy or an anticoagulant. A hemorrhage may be diagnosed by a suitable method, non-limiting examples of which include a CT scan, MRI scan or angiogram.

A hemorrhage may be an acute hemorrhage or chronic hemorrhage. A hemorrhage may be mild, moderate or severe. In some embodiment, a hemorrhage is a Class I, II, III or IV hemorrhage. In some embodiments, a Class I hemorrhage is classified, in part, by an estimation of blood loss that is less than ≤15% of total blood volume. In certain embodiments, a method herein comprises preventing, reducing a risk of, inhibiting, reducing, mitigating, and/or treating hemorrhage where the hemorrhage is a Class I hemorrhage, or where the estimated blood loss due to the hemorrhage is equal to or less than 15%, 10%, 5%, 2%, or 1% of total blood volume.

In certain embodiments, a method of inhibiting, reducing, mitigating, and/or treating hemorrhage comprises reducing hemorrhage volume. A method herein may reduce hemorrhage volume by at least 1%, at least 2%, at least 5%, at least 10%, at least 20%, at least 50%, at least 75%, or by at least 90%. In certain embodiments, a method herein may reduce hemorrhage volume by 1% to 100%, 1% to 75%, 1% to 50%, 1% to 25%, 1% to 20%, 1% to 10% or by 1% to 5%.

In some embodiments, hemorrhage comprises or consists of hemorrhage transformation. In some embodiments, hemorrhage transformation comprises hemorrhage transformation in the brain (e.g., cerebral hemorrhage transformation). Accordingly, in some embodiments, a method of preventing, reducing a risk of, inhibiting, reducing, mitigating, and/or treating hemorrhage comprises a method of preventing, reducing a risk of, inhibiting, reducing, mitigating, and/or treating hemorrhage transformation. In some embodiments, a method comprises preventing, reducing a risk of, inhibiting, reducing, mitigating, and/or treating hemorrhage transformation induced by a thrombolytic therapy or an anticoagulant.

Pharmaceutical Compositions

In some embodiments, a composition or pharmaceutical composition comprises a compound disclosed herein (e.g., a compound of Formula I, II, III or IV). In some embodiments, a composition or pharmaceutical composition comprises a compound disclosed herein and a tissue plasminogen activator (tPA), a streptokinase, a streptokinase activator or a urokinase. In some embodiments, a composition or pharmaceutical composition comprises a compound disclosed herein and an anticoagulant. In some embodiments, a composition or pharmaceutical composition comprises a compound disclosed herein and tPA. In some embodiments, a composition or pharmaceutical composition comprises a therapeutically effective amount of a compound disclosed herein. In some embodiments, a composition or pharmaceutical composition comprises a therapeutically effective amount of a compound disclosed herein and a therapeutically effective amount of an anticoagulant. In some embodiments, a composition or pharmaceutical composition comprises a therapeutically effective amount of a compound disclosed herein and a therapeutically effective amount of a tPA.

In some embodiments, a composition or pharmaceutical composition comprises a compound disclosed herein in an amount in a range of 1 µg to 1000 mg, 1 µg to 100 mg, or 10 µg to 100 µg. In some embodiments provided herein is a pharmaceutical composition comprising a compound disclosed herein for use in conducting a method described herein. In some embodiments, a pharmaceutical composition comprises a compound disclosed herein and a pharmaceutically acceptable excipient, diluent, additive or carrier.

A pharmaceutical composition can be formulated for a suitable route of administration. In some embodiments a pharmaceutical composition is formulated for oral, subcutaneous (s.c.), intradermal, intramuscular, intraperitoneal and/or intravenous (i.v.) administration. In certain embodiments, a pharmaceutical composition contains formulation materials for modifying, maintaining, or preserving, for example, the pH, osmolarity, viscosity, clarity, color, isotonicity, odor, sterility, stability, rate of dissolution or release, adsorption or penetration of the composition. In certain embodiments, suitable formulation materials include, but are not limited to, amino acids (such as glycine, glutamine, asparagine, arginine or lysine); antimicrobials; antioxidants (such as ascorbic acid, sodium sulfite or sodium hydrogensulfite); buffers (such as borate, bicarbonate, Tris-HCl, citrates, phosphates (e.g., phosphate buffered saline) or suitable organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counter ions (such as sodium); solvents (such as glycerin, propylene glycol or polyethylene glycol); diluents; excipients and/or pharmaceutical adjuvants. In particular, a pharmaceutical composition can comprise any suitable carrier, formulation, or ingredient, the like or combinations thereof as listed in "Remington: The Science And Practice Of Pharmacy" Mack Publishing Co., Easton, PA, $19^{th}$ Edition, (1995)(hereafter, Remington '95), or "Remington: The Science And Practice Of Pharmacy", Pharmaceutical Press, Easton, PA, $22^{nd}$ Edition, (2013)(hereafter, Remington 2013), the contents of which are incorporated herein by reference in their entirety.

In certain embodiments, a pharmaceutical composition comprises a suitable excipient, non-limiting examples of which include anti-adherents (e.g., magnesium stearate), a binder, fillers, monosaccharides, disaccharides, other carbohydrates (e.g., glucose, mannose or dextrin), sugar alcohols (e.g., mannitol or sorbitol), coatings (e.g., cellulose, hydroxypropyl methylcellulose (HPMC), microcrystalline cellulose, synthetic polymers, shellac, gelatin, corn protein zein, enterics or other polysaccharides), starch (e.g., potato, maize or wheat starch), silica, colors, disintegrants, flavors, lubricants, preservatives, sorbents, sweeteners, vehicles, suspending agents, surfactants and/or wetting agents (such as pluronics, PEG, sorbitan esters, polysorbates such as polysorbate 20, polysorbate 80, triton, tromethamine, lecithin, cholesterol, tyloxapal), stability enhancing agents (such as sucrose or sorbitol), and tonicity enhancing agents (such as alkali metal halides, sodium or potassium chloride, mannitol, sorbitol), and/or any excipient disclosed in Remington '95 or Remington 2013. The term "binder" as used herein refers to a compound or ingredient that helps keeps a pharmaceutical mixture combined. Suitable binders for making pharmaceutical formulations and are often used in the preparation of pharmaceutical tablets, capsules and granules are known to those skilled in the art.

In some embodiments a pharmaceutical composition comprises a suitable pharmaceutically acceptable additive and/or carrier. Non-limiting examples of suitable additives include a suitable pH adjuster, a soothing agent, a buffer, a sulfur-containing reducing agent, an antioxidant and the like. Non-limiting examples of a sulfur-containing reducing agent include those having a sulfhydryl group (e.g., a thiol) such as N-acetylcysteine, N-acetylhomocysteine, thioctic acid, thiodiglycol, thioethanolamine, thioglycerol, thiosorbitol, thioglycolic acid and a salt thereof, sodium thiosulfate, glutathione, and a C1-C7 thioalkanoic acid. Non-limiting examples of an antioxidant include erythorbic acid, dibutylhydroxytoluene, butylhydroxyanisole, alpha-tocopherol, tocopherol acetate, L-ascorbic acid and a salt thereof, L-ascorbyl palmitate, L-ascorbyl stearate, sodium bisulfite, sodium sulfite, triamyl gallate and propyl gallate, as well as chelating agents such as disodium ethylenediaminetetraacetate (EDTA), sodium pyrophosphate and sodium metaphosphate. Furthermore, diluents, additives and excipients may comprise other commonly used ingredients, for example, inorganic salts such as sodium chloride, potassium chloride, calcium chloride, sodium phosphate, potassium phosphate and sodium bicarbonate, as well as organic salts such as sodium citrate, potassium citrate and sodium acetate.

The pharmaceutical compositions used herein can be stable over an extended period of time, for example on the order of months or years. In some embodiments a pharmaceutical composition comprises one or more suitable preservatives. Non-limiting examples of preservatives include benzalkonium chloride, benzoic acid, salicylic acid, thimerosal, phenethyl alcohol, methylparaben, propylparaben, chlorhexidine, sorbic acid, hydrogen peroxide, the like and/or combinations thereof. A preservative can comprise a quaternary ammonium compound, such as benzalkonium chloride, benzoxonium chloride, benzethonium chloride, cetrimide, sepazonium chloride, cetylpyridinium chloride, or domiphen bromide (BRADOSOL®). A preservative can comprise an alkyl-mercury salt of thiosalicylic acid, such as thimerosal, phenylmercuric nitrate, phenylmercuric acetate or phenylmercuric borate. A preservative can comprise a paraben, such as methylparaben or propylparaben. A preservative can comprise an alcohol, such as chlorobutanol, benzyl alcohol or phenyl ethyl alcohol. A preservative can comprise a biguanide derivative, such as chlorohexidine or polyhexamethylene biguanide. A preservative can comprise sodium perborate, imidazolidinyl urea, and/or sorbic acid. A preservative can comprise stabilized oxychloro complexes, such as known and commercially available under the trade name PURITE®. A preservative can comprise polyglycol-polyamine condensation resins, such as known and commercially available under the trade name POLYQUART® from Henkel KGaA. A preservative can comprise stabilized hydrogen peroxide. A preservative can be benzalkonium chloride. In some embodiments a pharmaceutical composition is free of preservatives.

In some embodiments a composition, pharmaceutical composition or compound disclosed herein is substantially free of contaminants (e.g., blood cells, platelets, polypeptides, minerals, blood-borne compounds or chemicals, virus, bacteria, other pathogens, toxin, and the like). In some embodiments a composition, pharmaceutical composition or compound disclosed herein is substantially free of serum and serum contaminants (e.g., serum proteins, serum lipids, serum carbohydrates, serum antigens and the like). In some embodiments a composition, pharmaceutical composition or compound disclosed herein is substantially free of a pathogen (e.g., a virus, parasite or bacteria). In some embodiments a composition, pharmaceutical composition or compound disclosed herein is substantially free of endotoxin. In some embodiments a composition, pharmaceutical composition or compound disclosed herein is sterile. In certain embodiments, a composition or pharmaceutical composition disclosed herein comprises a compound of Formula I, II, III or IV.

The pharmaceutical compositions described herein may be configured for administration to a subject in any suitable form and/or amount according to the therapy in which they are employed. For example, a pharmaceutical composition configured for parenteral administration (e.g., by injection or infusion), may take the form of a suspension, solution or emulsion in an oily or aqueous vehicle and it may contain formulation agents, excipients, additives and/or diluents such as aqueous or non-aqueous solvents, co-solvents, suspending solutions, preservatives, stabilizing agents and or dispersing agents. In some embodiments a pharmaceutical composition suitable for parenteral administration may contain one or more excipients. In some embodiments a pharmaceutical composition is lyophilized to a dry powder form. In some embodiments a pharmaceutical composition is lyophilized to a dry powder form, which is suitable for reconstitution with a suitable pharmaceutical solvent (e.g., water, saline, an isotonic buffer solution (e.g., PBS), DMSO, combinations thereof and the like). In certain embodiments, reconstituted forms of a lyophilized pharmaceutical composition are suitable for parenteral administration (e.g., intravenous administration) to a mammal.

In certain embodiments, a pharmaceutical composition is configured for oral administration and may be formulated as a tablet, microtablet, minitablets, micropellets, powder, granules, capsules (e.g., capsules filled with microtablets, micropellets, powders or granules), emulsions, solutions, the like or combinations thereof. Pharmaceutical compositions configured for oral administration may comprise suitable coatings to delay or sustain release of the active ingredient, non-limiting examples of which include enteric coatings such as fatty acids, waxes, shellac, plastics, methyl acrylate-methacrylic acid copolymers, cellulose acetate phthalate (CAP), cellulose acetate succinate, hydroxypropyl methyl cellulose phthalate, hydroxypropyl methyl cellulose acetate succinate (hypromellose acetate succinate), polyvinyl acetate phthalate (PVAP), methyl methacrylate-methacrylic acid copolymers, cellulose acetate trimellitate, sodium alginate, zein, plant fibers, the like and combinations thereof.

In some embodiments a pharmaceutical compositions described herein may be configured for topical administration and may include one or more of a binding and/or lubricating agent, polymeric glycols, gelatins, cocoa-butter or other suitable waxes or fats. In some embodiments a pharmaceutical composition described herein is incorporated into a topical formulation containing a topical carrier that is generally suited to topical drug administration and comprising any suitable material known to those skilled in the art. In certain embodiments, a topical formulation of a pharmaceutical composition is formulated for administration of a compound using a topical patch.

In certain embodiments, an optimal pharmaceutical composition is determined by one skilled in the art depending upon, for example, on the intended route of administration, delivery format and desired dosage (see e.g., Remington '95 or Remington 2013, supra). A pharmaceutical composition can be manufactured by any suitable manner, including, e.g., by means of conventional mixing, dissolving, granulating, dragee-making, levigating, emulsifying, encapsulating, entrapping or tableting processes (e.g., see methods described in Remington '95 or Remington 2013).

Route of Administration

Any suitable method of administering a composition, pharmaceutical composition or compound disclosed herein to a subject can be used. Any suitable formulation and/or route of administration can be used for administration of a compound disclosed herein or composition disclosed herein (e.g., see Fingl et al. 1975, in "The Pharmacological Basis of Therapeutics", which is incorporated herein by reference in its entirety). A suitable formulation and/or route of administration can be chosen by a medical professional (e.g., a physician) in view of, for example, a subject's risk, age, and/or condition. Non-limiting examples of routes of administration include topical or local (e.g., transdermally or cutaneously, (e.g., on the skin or epidermis), in or on the eye, intranasally, transmucosally, in the ear, inside the ear (e.g., behind the ear drum)), enteral (e.g., delivered through the gastrointestinal tract, e.g., orally (e.g., as a tablet, capsule, granule, liquid, emulsification, lozenge, or combination thereof), sublingual, by gastric feeding tube, rectally, and the like), by parenteral administration (e.g., parenterally, e.g., intravenously, intra-arterially, intramuscularly, intraperitoneally, intradermally, subcutaneously, intracavity, intracranial, intra-articular, into a joint space, intracardiac (into the heart), intracavernous injection, intralesional (into a skin lesion), intraosseous infusion (into the bone marrow), intrathecal (into the spinal canal), intrauterine, intravaginal, intravesical infusion, intravitreal), the like or combinations thereof.

In some embodiments a compound disclosed herein or pharmaceutical composition described herein is administered to the lungs, bronchial passages, trachea, esophagus, sinuses, or nasal passages using a suitable method, non-limiting examples of which include intranasal administration, intratracheal instillation, and oral inhalative administration (e.g., by use of an inhaler, e.g., single/-multiple dose dry powder inhalers, nebulizers, and the like).

In some embodiments a compound disclosed herein or a pharmaceutical composition disclosed herein is provided to a subject. For example, a composition that is provided to a subject is sometimes provided to a subject for self-administration or for administration to a subject by another (e.g., a non-medical professional). As another example, a composition can be provided as an instruction written by a medical practitioner that authorizes a patient to be provided a composition or treatment described herein (e.g., a prescription). In yet another example, a composition can be provided to a subject where the subject self-administers a composition orally, intravenously or by way of an inhaler, for example.

Alternately, one can administer a compound disclosed herein or composition in a local rather than systemic manner, for example, via direct application to the skin, mucous membrane or region of interest for treating, including using a depot or sustained release formulation.

In certain embodiments a pharmaceutical composition comprising a compound disclosed herein is administered alone (e.g., as a single active ingredient (AI or e.g., as a single active pharmaceutical ingredient (API)). In other embodiments, a pharmaceutical composition comprising a compound disclosed herein is administered in combination with one or more additional AIs/APIs, for example, as two separate compositions or as a single composition where the one or more additional AIs/APIs are mixed or formulated together with a compound disclosed herein in a pharmaceutical composition.

Dose and Therapeutically Effective Amount

In some embodiments, an amount of a compound disclosed herein, an amount of a thrombolytic drug, or amount of an anticoagulant (e.g., in a pharmaceutical composition) is a therapeutically effective amount. In certain embodiments, a pharmaceutical composition comprises a therapeutically effective amount of a compound, drug or agent disclosed herein. In some embodiments, a therapeutically effective amount of a compound, drug or agent disclosed herein is administered to a subject. In some embodiments, a therapeutically effective amount of a compound, drug or agent disclosed herein is an amount needed to obtain an effective therapeutic outcome. In certain embodiments, a therapeutically effective amount of a compound disclosed herein is an amount sufficient to treat or prevent hemorrhage or vascular instability. Determination of a therapeutically effective amount is well within the capability of those skilled in the art, especially in light of the detailed disclosure provided herein.

In certain embodiments, a therapeutically effective amount is an amount high enough to provide an effective therapeutic effect (e.g., a beneficial therapeutic effect) and an amount low enough to minimize unwanted adverse reactions. Accordingly, in certain embodiments, a therapeutically effective amount of a compound disclosed herein may vary from subject to subject, often depending on age, weight, general health condition of a subject and severity of a condition being treated. Thus, in some embodiments, a therapeutically effective amount is determined empirically. Accordingly, a therapeutically effective amount of a compound that is administered to a subject can be determined by one of ordinary skill in the art based on amounts found effective in animal or clinical studies, a physician's experience, and suggested dose ranges or dosing guidelines, for example.

In certain embodiments, a therapeutically effective amount of a compound disclosed herein is administered at a suitable dose (e.g., at a suitable volume, frequency and/or concentration, which often depends on a subject's weight, age and/or condition) intended to obtain an acceptable therapeutic outcome. In certain embodiments, a therapeutically effective amount of a compound comprises one or more doses selected from at least 0.01 mg/kg (e.g., mg of a compound per kg body weight of a subject), at least 0.1 mg/kg, at least 0.5 mg/kg, at least 1 mg/kg, at least 10 mg/kg or at least 100 mg/kg. In certain embodiments, a therapeutically effective amount of a compound is selected from one or more doses of about 0.001 mg/kg (e.g., mg of a compound per kg body weight of a subject) to about 5000 mg/kg, 0.01 mg/kg to 1000 mg/kg, 0.01 mg/kg to 500 mg/kg, 0.1 mg/kg to 1000 mg/kg, 1 mg/kg to 1000 mg/kg, 10 mg/kg to 1000 mg/kg, 100 mg/kg to 1000 mg/kg, 0.1 mg/kg to 500 mg/kg, 0.1 mg/kg to 250 mg/kg, 0.1 mg/kg to 150 mg/kg, 0.1 mg/kg to 100 mg/kg, 0.1 mg/kg to 75 mg/kg, 0.1 mg/kg to 50 mg/kg, 0.1 mg/kg to 25 mg/kg, 0.1 mg/kg to 10 mg/kg, 0.1 mg/kg to 5 mg/kg, 0.5 mg/kg to 5 mg/kg, intervening amounts and combinations thereof. In some aspects a therapeutically effective amount of a compound administered to a subject comprises one or more doses of about 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 50 mg/kg, 100 mg/kg, 500 mg/kg, and intervening amounts and combinations thereof. In some embodiments a therapeutically effective amount of a compound disclosed herein is between about 0.1 mg/kg and about 50 mg/kg, between about 1 mg/kg and about 50 mg/kg, or between about 1 mg/kg and about 30 mg/kg.

In certain embodiments, a therapeutically effective amount of tPA is administered at a suitable dose (e.g., at a suitable volume, frequency and/or concentration, which often depends on a subject's weight, age and/or condition) intended to obtain an acceptable therapeutic outcome. In some embodiments, tPA is administered at a dose of 0.1 mg/kg to 1.5 mg/kg. As disclosed herein tPA, when administered with a compound disclosed herein, can be administered at higher dose, since compounds disclosed herein can inhibit or mitigate the adverse reactions of tPA. Accordingly, in some embodiments, tPA is administered at a dose of 0.1 mg/kg to 100 mg/kg, at 0.1 mg/kg to 50 mg/kg, 0.1 mg/kg to 30 mg/kg, 0.1 mg/kg to 20 mg/kg, or 0.1 mg/kg to 5 mg/kg. In some embodiments, tPA is administered at a dose of 1.0 mg/kg to 100 mg/kg, at 1.0 mg/kg to 50 mg/kg, 1.0 mg mg/kg to 30 mg/kg, 1.0 mg/kg to 20 mg/kg, or 1.0 mg mg/kg to 5 mg/kg. In some embodiments, tPA is administered at a dose of 1.5 mg/kg to 100 mg/kg, 1.5 mg/kg to 50 mg/kg, 1.5 mg mg/kg to 30 mg/kg, 1.5 mg/kg to 20 mg/kg, or 1.5 mg mg/kg to 5 mg/kg. In some embodiments, tPA is administered at a dose of about 1.6 mg/kg to 100 mg/kg, 1.8 mg/kg to 100 mg/kg, 2.0 mg/kg to 100 mg/kg, 1.6 mg/kg to 50 mg/kg, 1.8 mg/kg to 50 mg/kg, 2.0 mg/kg to 500 mg/kg, 1.6 mg/kg to 30 mg/kg, 1.8 mg/kg to 30 mg/kg, 2.0 mg/kg to 30 mg/kg, 1.6 mg/kg to 20 mg/kg, 1.8 mg/kg to 20 mg/kg, 2.0 mg/kg to 20 mg/kg, 1.6 mg/kg to 5 mg/kg, 1.8 mg/kg to 5 mg/kg, or 2.0 mg/kg to 5 mg/kg. In some embodiments, tPA is administered in combination with a compound disclosed herein. In some embodiments, tPA is administered substantially at the same time as, or before administration of a compound disclosed herein. Substantially at the same time means that tPA and a compound disclosed herein are administered within a time period of 30 minutes. In some embodiments, tPA is administered after administration of a compound disclosed herein. In certain embodiments, a dose of tPA can be administered with a compound disclosed herein at a dose that is greater than 20 mg, greater than 30 mg, greater than 40 mg, greater than 50 mg, greater than 90 mg, greater than 100 mg or greater than 110 mg when administered as a bolus dose, or by infusion over a period of 30 minutes to 10 hours, or 30 minutes to 2 hours.

In some embodiments administering a therapeutically effective amount of a compound disclosed herein, or a pharmaceutical composition comprising a compound disclosed herein, comprises administering a suitable dose at a frequency or interval as needed to obtain an effective therapeutic outcome. In some embodiments administering a therapeutically effective amount of a compound or a pharmaceutical composition disclosed herein comprises administering a suitable dose hourly, every two hours, every 4 hours, every 6 hours, three times a day, twice a day, once a day, six times a week, five times a week, four times a week, three times a week, twice a week, weekly, at combinations thereof, and/or at regular or irregular intervals thereof, and/or simply at a frequency or interval as needed or recommended by a medical professional. In some embodiments, a therapeutically effective amount of a compound or pharmaceutical composition is administered continuously by, for example by intravenous administration.

In some embodiments a therapeutically effective amount of a compound is administered to a subject prior to, during and/or after a subject receives a thrombolytic, anti-coagulant or endovascular intervention therapy. In some embodiments a therapeutically effective amount of a compound is administered to a subject up to 3 days prior to, up to 2 days prior to, up to 1 day prior to, up to 20 hours prior to, up to 15 hours prior to, up to 10 hours prior to, up to 5 hours prior to, up to 2 hours prior to or up to 1 hour prior to administration of a thrombolytic, anti-coagulant or endovascular intervention therapy. In some embodiments a therapeutically effective amount of a compound is administered to a subject 0 to 72 hours, 0 and 48 hours, 0 to 24 hours, 0 to 12 hours, 0 to 6 hours, 0 to 4 hours, or 0 to 2 hours before administration of a thrombolytic, anti-coagulant or endovascular intervention therapy. In some embodiments a therapeutically effective amount of a compound is administered during, or concurrently with, administration of a thrombolytic, anti-coagulant or endovascular intervention therapy. In some embodiments a therapeutically effective amount of a compound is administered intermittently or continuously for up to 1 hour after, 2 hours after, 4 hours after, 6 hours after, 12 hours after, 24 hours after, 2 days after, 3 days after, a week after, 1 month after, 3 months after, 6 months after, 12 months after, 18 months after, 24 months after or up to 36 months administration of a thrombolytic, anti-coagulant or endovascular intervention therapy.

In some embodiments, a therapeutically effective amount of a compound described herein is administered 1 hour to 1 week after administration of the thrombolytic therapy, or intervening ranges thereof. In certain embodiments, a therapeutically effective amount of a compound described herein is administered 1 to 48 hours, 2 to 48 hours or 4 to 48 hours, after administration of the thrombolytic therapy.

In some embodiments a thrombolytic therapy comprises administration of tissue plasminogen activator (tPA). tPA is often administered within a time period of 30 seconds to 3.5 hours after a subject experiences an ischemic stroke. However, tPA administration can cause adverse and sometimes lethal side effects such as hemorrhage, vascular instability and disruption of the blood brain barrier. As disclosed herein, administration of a compound described herein can prevent, reduce the risk of, inhibit the severity of, reduce, mitigate and/or treat hemorrhage associated with tPA administration. Accordingly, in some embodiments, a therapeutically effective amount of a compound described herein is administered concurrently with, within 0 to 48 hours after, or up to 1-3 weeks after tPA administration. In some embodiments, a therapeutically effective amount of a compound described herein is administered 1 to 24 hours, 2 to 24 hours, 3 to 24 hours, 3.5 to 24 hours, or 4 to 24 hours after tPA administration. In some embodiments, a therapeutically effective amount of a compound described herein is administered 0 to 8 hours, 0 to 6 hours or 0 to 4 hours after tPA administration.

Kits

In some embodiments, provided herein is a kit comprising (i) a compound disclosed herein, (ii) a thrombolytic drug or agent, and/or (iii) an anticoagulant, or a pharmaceutical composition comprising one or more of (i), (ii) and (iii). In some embodiments, a kit comprises one or more doses of a (i) a compound disclosed herein, (i) one or more doses of a thrombolytic drug or agent, and/or (iii) one or more doses of an anticoagulant. In some embodiments, a kit comprises one or more doses of a pharmaceutical composition comprising (i) a compound disclosed herein, (i) a thrombolytic drug or agent, and/or (iii) an anticoagulant. In some embodiments, a kit comprises one or more packs and/or one or more dispensing devices, which can contain one or more doses of a compound disclosed herein, or a pharmaceutical composition described herein. Non-limiting examples of a pack include a metal, glass, or plastic container, syringe or blister pack that comprises a compound disclosed herein or a composition described herein. In certain embodiments, a kit comprises a dispensing device such as a syringe or inhaler, that may or may not comprise a compound disclosed herein or a composition described herein. A pack and/or dispenser device can be accompanied by instructions for administration. The pack or dispenser can also be accompanied with a notice associated with the container in a form prescribed by a governmental agency regulating the manufacture, use, or sale of pharmaceuticals, which notice is reflective of approval by the agency of the form of the drug for human or veterinary administration. Such notice, for example, can be the labeling approved by the U.S. Food and Drug Administration for prescription drugs, or the approved product insert.

In some embodiments a kit or pack comprises an amount of a compound disclosed herein sufficient to treat a patient for 1 day to 1 year, 1 day to 180 days, 1 day to 120 days, 1 day to 90 days, 1 day to 60 days, 1 day to 30 days, 1-24 hours, 1-12 hours, 1-4 hours, or amount of time there between.

A kit optionally includes a product label and/or one or more packaging inserts, that provide a description of the components or instructions for use in vitro, in vivo, or ex vivo, of the components therein. Exemplary instructions may include instructions for a treatment protocol or therapeutic regimen. In certain embodiments, a kit comprises packaging material, which refers to a physical structure housing components of the kit. The packaging material can maintain the components sterilely and can be made of material commonly used for such purposes (e.g., paper, corrugated fiber, glass, plastic, foil, ampules, vials, tubes, etc.). Product labels or inserts include "printed matter," e.g., paper or cardboard, or separate or affixed to a component, a kit or packing material (e.g., a box), or attached to an ampule, tube or vial containing a kit component. Labels or inserts can additionally include a computer readable medium, optical disk such as CD- or DVD-ROM/RAM, DVD, MP3, magnetic tape, or an electrical storage media such as RAM and ROM or hybrids of these such as magnetic/optical storage media, FLASH media or memory-type cards. Product labels or inserts can include identifying information of one or more components therein, dose amounts, clinical pharmacology of the active ingredient(s) including mechanism of action, pharmacokinetics (PK) and pharmacodynamics (PD). Product labels or inserts can include information identifying manufacturer information, lot numbers, manufacturer location, date, information on an indicated condition, disorder, disease or symptom for which a kit component may be used. Product labels or inserts can include instructions for the clinician or for a subject for using one or more of the kit components in a method, treatment protocol or therapeutic regimen. Instructions can include dosage amounts, frequency or duration, and instructions for practicing any of the methods, treatment protocols or therapeutic regimes set forth herein. A kit can additionally include labels or instructions for practicing any of the methods described herein. Product labels or inserts can include information on potential adverse side effects and/or warnings.

EXAMPLES

Example 1—Suture Transient MCAO Model

A suture-type transient middle cerebral artery occlusion (MCAO) model was used to determine the efficacy and dose response of J147 (Compound IV) on reperfusion using male Sprague Dawley rats having a body weight in a range of 280-320 g. In this model, J147 was administered i.v. at doses of 1 mg/kg, 10 mg/kg and 30 mg/kg of total body weight immediately after reperfusion (i.e., about 2 hours after ischemia onset). A dose of 10 mg/kg (iv) was considered as an optimal effective dose in this study.

Suture transient MCAO model
SD rat: 280 to 320 g
Stroke mode: suture, Ischemia for 2 hours followed by Reperfusion for 24 hours
Bederson scale* (tested at 24 hours after reperfusion): 0 to 5, less to more behavioral neurological deficits
J147: administered immediately after reperfusion
J147 stocking solution: 6 mg/ml, 30% HS15/70% saline
J147 working solution: stock solution/saline 1:1 (3 mg/ml, 15% HS15/85% saline)
Vehicle: 15% HS15/85% saline
  iv injection (bolus): 3.3 ml/kg body weight.
  ip injection (bolus): 10 ml/kg body weight
Rat: Maximum volume (iv., bolus)=5 ml/kg. (ip., bolus) =10 ml/kg.

Following stroke, animals exhibit a variety of neurological deficits. The Bederson scale is a global neurological assessment that was developed to measure neurological impairments following stroke. Tests include forelimb flexion, resistance to lateral push and circling behavior. In this case, a Bederson grading scale of 0-5 was used to assess behavioral deficits after reperfusion. This scoring scale is a simple way to reveal basic neurological deficits. Ischemic animals will have significantly more neurological deficits than non-ischemic animals, resulting in a higher score.

Results are shown in FIG. 1. Representative images (chosen from the median animals of each group) of triphenyl tetrazolium chloride (TTC)-stained brain coronal sections A-H showing tissue infarction (white color) in the indicated groups 24 hours after reperfusion. Panels A&B are control animals treated with placebo and showing Bederson Scores 3 and 5, and significant infarct volume (white) after reperfusion. Panels C&D are animals treated with 1 mg/kg J147 administered intravascularly (iv), showing better Bederson Scores of 3 and 3, and insignificant reduction in infarct volume relative to placebo. Panels E&F are animals treated with 10 mg/kg J147 administered iv, showing much improved Bederson scores of 1 and 2, and a large reduction of infarct volume after reperfusion. Panels G&H are animals treated with J147 administered intraperitoneally, showing Bederson scores of 2 and 3, and modest reduction of infarct volume after reperfusion.

Example 2—Embolic MCAO Model

For embolic MCAO model (eMCAO), a single 4 μm fibrin rich clot was placed in the origin of the right MCA via a modified PE-50 tube (0.3-mm outer diameter). Regional cerebral blood flow (rCBF) in the MCA territory (2 mm posterior and 5 mm lateral to the bragma on the right parietal skull) was monitored with Laser doppler flowmetry (MSP300XP; ADInstruments Inc). The animals' rCBF reduction to 25% or less of baseline level was included in the study.

Figure 4A:
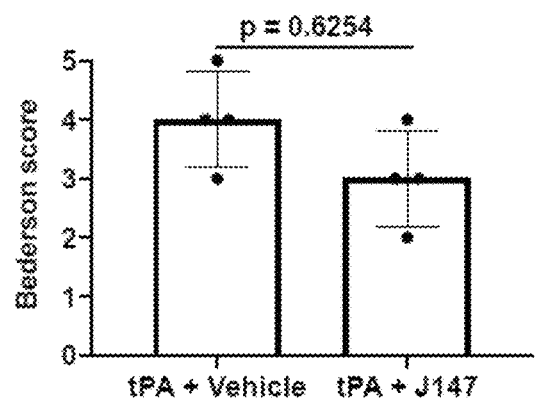
FIG. 4A shows a graph of Bederson scores showing a positive trend in tPA+J147-treated vs tPA-only treated animals (p=0.6254).
Figure 4B:
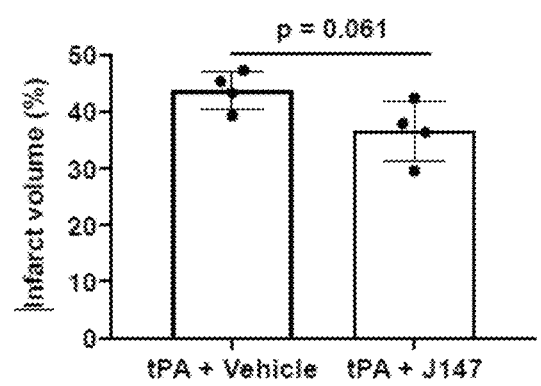
FIG. 4B shows a graph of scan-quantified infarct volume showing a positive trend in tPA+J147-treated animals (p=0.061).
Figure 4C:
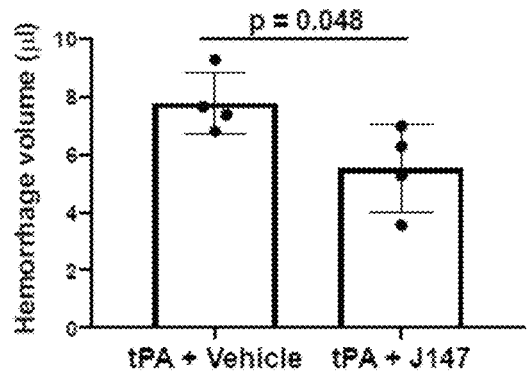
FIG. 4C shows a graph of quantified hemorrhage volume showing a significant improvement in tPA+J147-treated animals (p=0.048).

Combined treatment: J147+tPA, tissue plasminogen activator, the only drug approved by the FDA for the treatment of stroke.
SD rat: 280 to 320 g
Stroke mode: eMCAO, 4 μm blood clot
Bederson scale (tested at 24 hour after ischemia): 0 to 5
J147 (10 mg/kg: 5% DMSO, 70% PEG200 and 25% Saline): at 4 h after ischemia onset (iv infusion for 1 min)
tPA (10 mg/kg (2 mg/ml)): at 4 hour after ischemia onset 10% bolus for 1 min., 90% infused for 30 min.
Two groups: tPA-only treated and tPA+J147-treated Results are shown in FIG. 2 (animals treated with tPA only) and FIG. 3 (Animals treated with tPA+J147). Representative images are shown (chosen from the median animals of each group) of unstained coronal sections (A, C, E, G) showing intracerebral hemorrhage (red color) and TTC-stained coronal sections (B, D, F, H) showing tissue infarction (white color) in the indicated groups 24 hours after stroke. FIG. 4A shows a graphical plot of Bederson scores showing positive trend in tPA+J147-treated vs tPA-only treated animals (p=0.6254). FIG. 4B shows a graphical plot of scan-quantified infarct volume showing positive trend in tPA+J147-treated animals (p=0.061). FIG. 4C shows a graphical plot of quantified hemorrhage volume showing a significant improvement in tPA+J147-treated animals (p=0.048).

Example 3—J147 Dose-Response (Expanded Study)

Objective: This experiment was performed to determine dose-dependent therapeutic effects of J147, and to identify an optimal dose.

J147 stock solution: 6 mg/ml in 30% HS15/170% saline
J147 working solution: 3 mg/ml in 15% HS15/85% saline (stock solution/saline 1:1)
Vehicle: 15% HS15/85% saline
Male SD rats; n=7-8 per group.

Figure 5A:
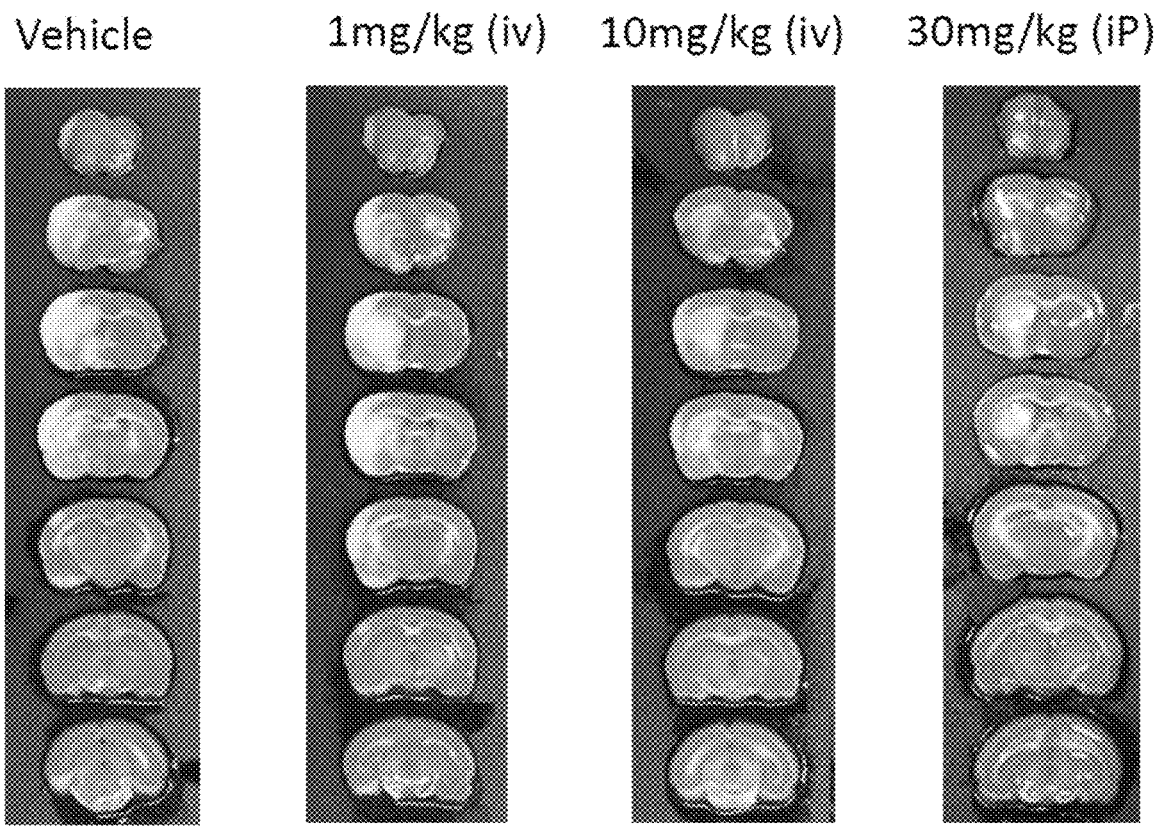
FIG. 5A shows TTC-stained coronal sections of brain isolated from rats treated with vehicle or J147. Red color indicates normal tissue and white color indicates tissue infarction (white color) in the indicated groups. Rats were subjected to 2-hour ischemia followed by reperfusion. Infarct volume (FIG. 5C) and Bederson scores (FIG. 5B) were assessed 72 hours after stroke. (n=7-8 per group). The * symbol indicates P<0.05.
Figure 5B:
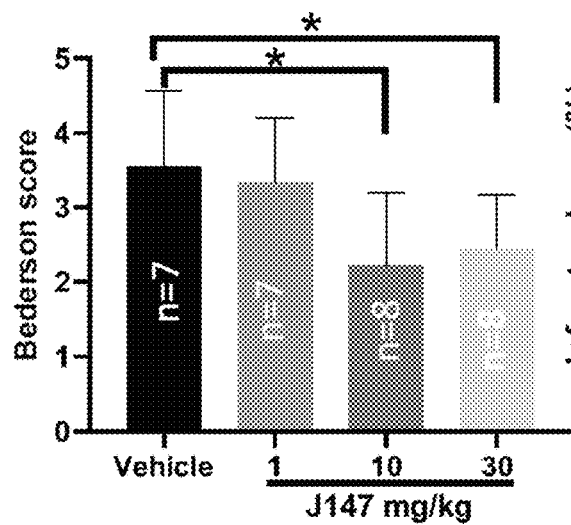
Figure 5C:
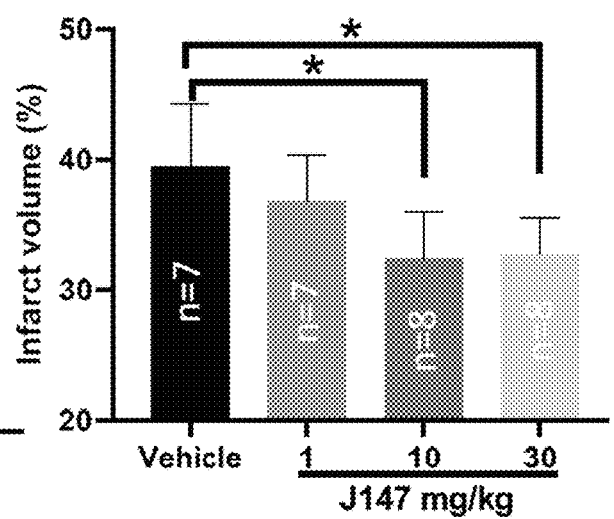
Figure 6A:
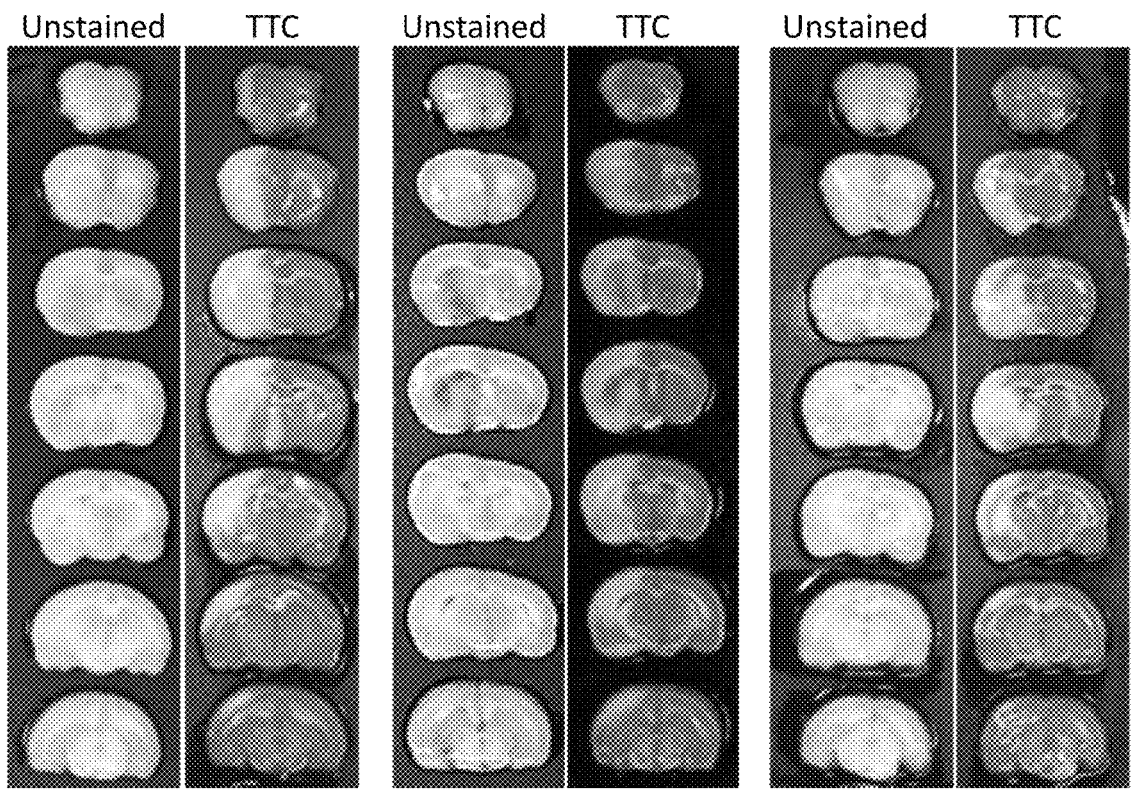
FIG. 6A shows unstained and TTC-stained coronal sections of brain isolated from rats treated with saline, tPA+ vehicle or tPA+J147. Red color in TTC stained sections indicates normal tissue and white color indicates tissue infarction in the indicated groups. Rats were subjected to 2-hour ischemia followed by reperfusion. Infarct volume (FIG. 6C), Bederson scores (FIG. 6B) and blood volume (FIG. 6D) were assessed 72 hours after stroke. (n=7-8 per group). The * symbol indicates P<0.05.
Figure 6B:
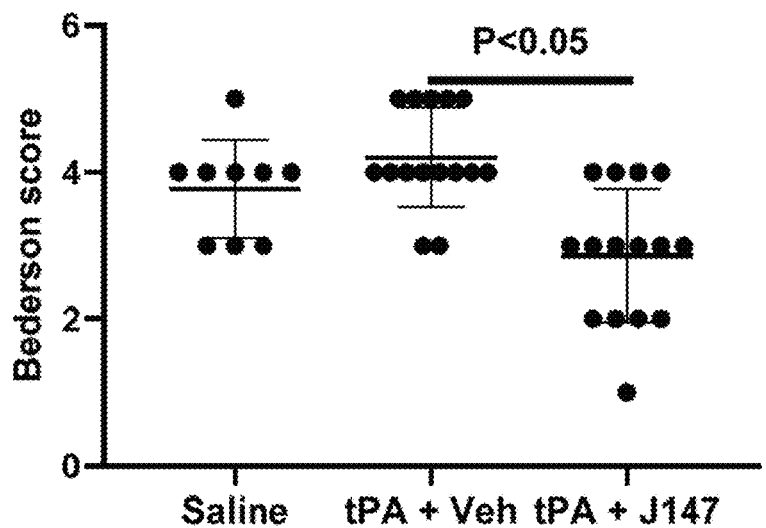
Figure 6C:
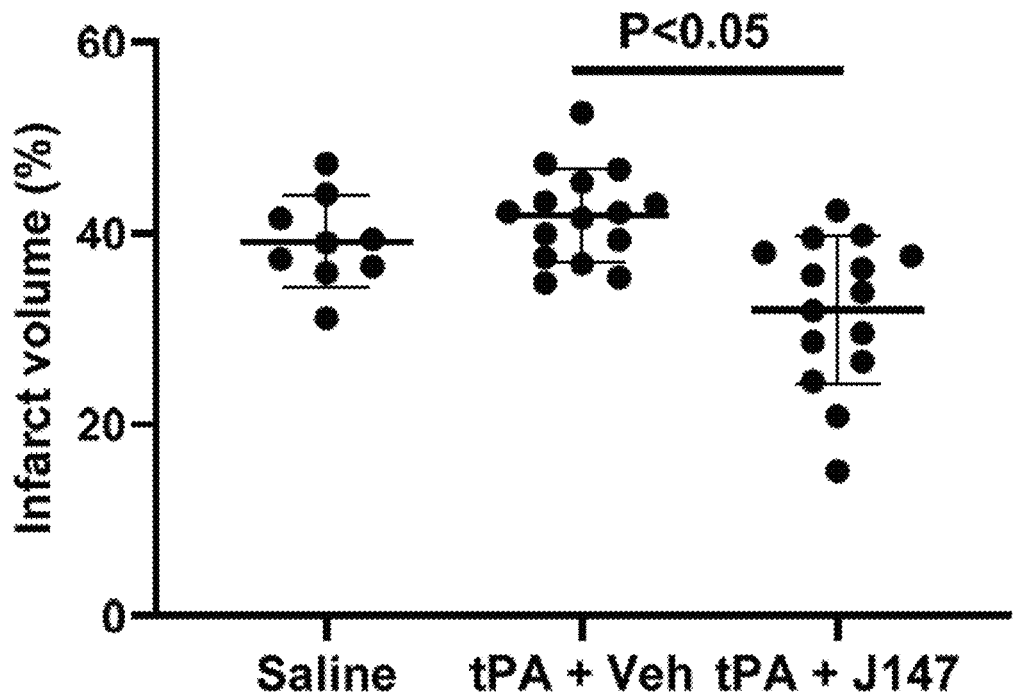
Figure 6D:
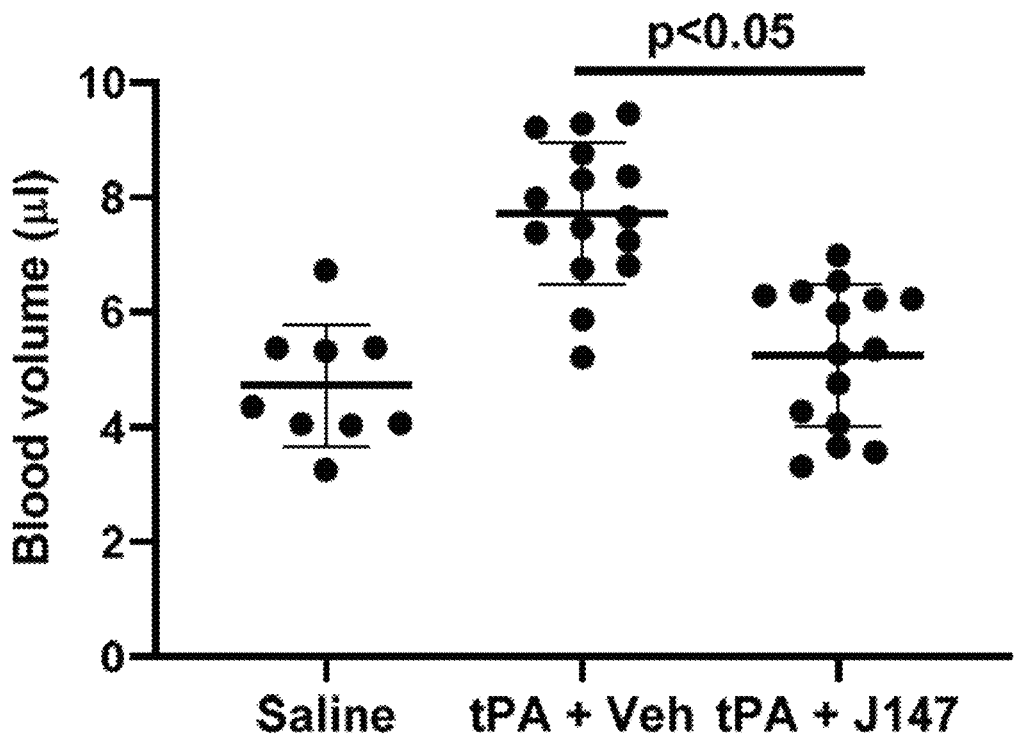
Figure 7A:
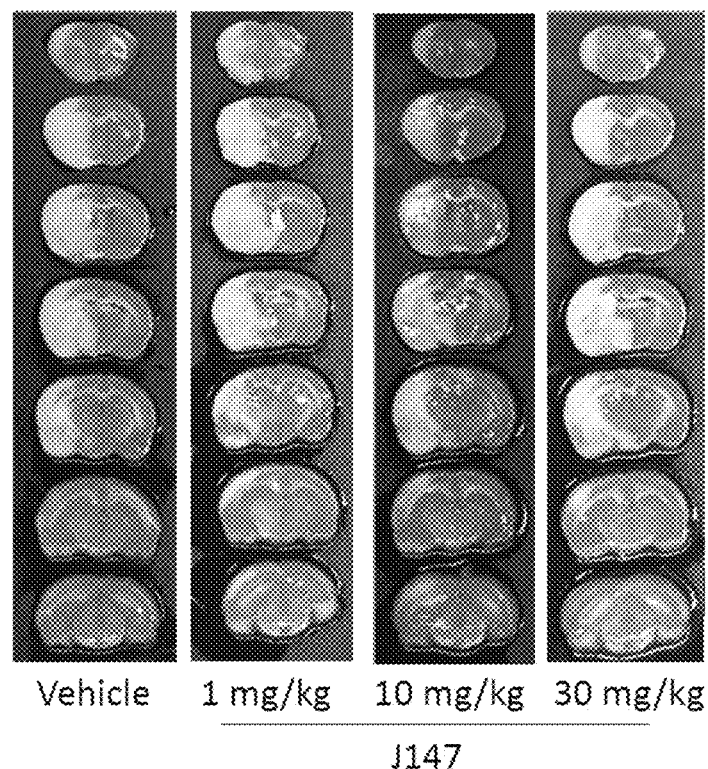
FIG. 7A shows TTC-stained coronal sections of brain isolated from rats treated with vehicle or J147. Red color indicates normal tissue and white color indicates tissue infarction (white color) in the indicated groups. Rats were subjected to 2-hour ischemia followed by reperfusion.
Figure 7B:
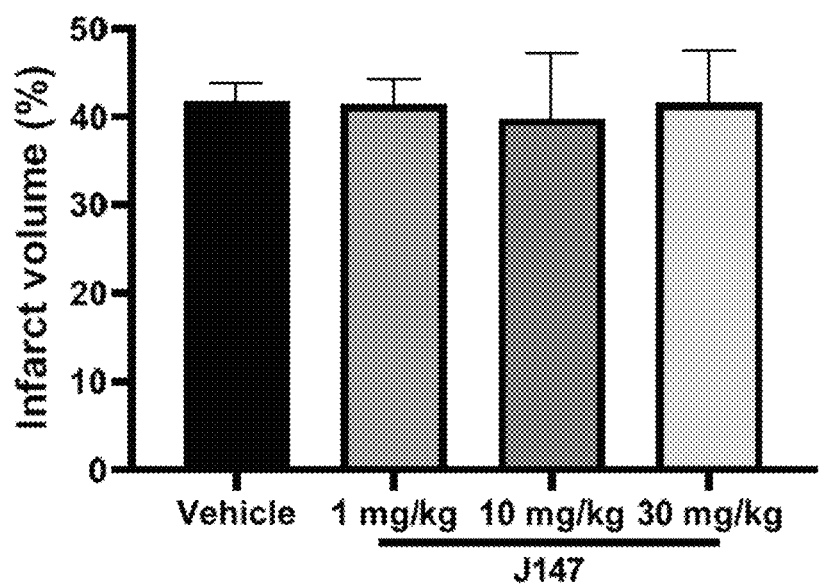
FIG. 7B shows a graphical representation of infarct volume (%) assessed 72 hours after stroke for the experiment of 7A. (n=7-8 per group).

Methods: Male SD rats (280-300 g) were subjected to a 2-hour suture MCAO-induced ischemia followed by reperfusion. J147 compound (1.0, 10, 30 mg/kg) and vehicle were administered at 2 hours after onset of ischemia (FIG. 5). Bederson score was examined prior to the sacrifice at 72 h after stroke. Infarct volumes in TTC-stained brain coronal sections were measured. Results: J147 treatment significantly reduced infarct volumes and neurological deficit after reperfusion in a dose-dependent manner. A dose of 10 mg/kg J147 is selected as an "effective optimal dose" for the treatment of acute ischemic stroke in rats.

Example 4—J147+tPA Expanded Study (~80 Animals)

Objective: To determine whether J147 can prevent tPA-associated brain hemorrhage and extend the treatment time window of tPA in a clinically relevant thromboembolic stroke model in rats.

J147 compound: Stock solution: 60 mg/ml DMSO, in 60 ul/vial, stored at −20° C.
Working solution: 3 mg/ml in 5% DMSO, 70% PEG200 and 25% normal saline, prepared prior to injection.
One vial stock solution was warmed at 37° C. and mixed with 1140 ul sterilized solution (PEG200: saline, 2.8:1).
Recombinant human tPA (Alteplase, 2.2 mg/vial): Reconstituted with 1.1 ml water (2 mg/ml). 10 mg/kg, 10% bonus injection, 90% 30 min. via mini pump.

A. Infarct Volume and Intracerebral Hemorrhage

Methods: Male SD rats (280-300 g) were subjected to thromboembolic middle cerebral artery occlusion (MCAO) and treated with saline at 4 hours, tPA (tissue-type plasminogen activator; 10 mg/kg, IV) at 4 hours, and combined J147 (10 mg/kg, IV) plus tPA at 4 hours after onset of ischemia. Bederson score was examined prior to the sacrifice at 72 h after stroke. Infarct volumes, brain hemorrhage, and animal mortality were measured.

Results: tPA treatment at 4 hours alone did not decrease brain infarction but instead worsened hemorrhagic transformation. Combining J147 with tPA reduced infarct volume and ameliorated brain hemorrhage (FIG. 6A-6D). The mortality rate in saline and tPA alone treatment groups were 25% (3 of 12 rats) and 32% (7 of 22 rats), respectively. The mortality rate was reduced to 12% in combination treatment group (TABLE 1).

Conclusion: J147 plus tPA combination treatment attenuates tPA-associated hemorrhage and alleviates brain damage after eMCAO. Consequently, the use of J147 in combination with tPA may extend the length of the therapeutic window for administration of tPA following an ischemic event and thereby increase the number of stroke patients that could benefit from use of tPA.

J147 compound: Stock solution: 60 mg/ml DMSO, in 60 ul/vial, stored at −20° C.

Working solution: 3 mg/ml in 5% DMSO, 70% PEG200 and 25% normal saline, prepared prior to injection. One vial stock solution was warmed at 37° C. and mixed with 1140 ul sterilized solution (PEG200: saline, 2.8:1).

Recombinant human tPA (Alteplase, 2.2 mg/vial): Reconstituted with 1.1 ml water (2 mg/ml). 10 mg/kg, 10% bonus injection, 90% 30 min. via mini pump.

TABLE 1

Mortality Rates

| Group | Saline at 4 h<br>n = 12 | tPA at 4 h<br>n = 22 | J147 plus tPA at 4 h<br>n = 17 |
|---|---|---|---|
| Death (mortality rate) | 3 (25%) | 7 (32%) | 2 (12%)* | log-rank test *p < 0.05 vs Saline or tPA alone group

Example 5—J147 Alone with Embolic MCAO (eMCAO) Model

In this example, an eMCAO experiment was performed to determine if J147 alone (i.e., without administration of TPA or other thrombolytic intervention) provided any therapeutic benefit for stroke in the absence of reperfusion caused by TPA.

SD rats: 280 to 320 g

Stroke mode: eMCAO, 4 μm blood clot

Bederson scale (tested at 24 hour after ischemia): 0 to 5

No tPA treatment.

J147 administered a 0 mg/ml (Vehicle), 1 mg/ml or 10 mg/ml i.v., or 30 mg/ml i.p. two hours after stroke onset. (n-5/group)

J147 stocking solution: 6 mg/ml (30% HS15/70% saline)

J147 working solution: stock solution/saline 1:1 (3 mg/ml, 15% HS15/85% saline)

Vehicle: 15% HS15/85% saline

In this example, an eMCAO experiment was performed to determine if J147 alone provided any therapeutic benefit for stoke in the absence of reperfusion. In this example the animals were treated with vehicle or J147 in the absence of reperfusion or TPA treatment. Results are shown in FIG. 6. Representative images are shown (chosen from the median animals of each group) of TTC-stained coronal sections showing tissue infarction (white color) in the indicated groups 24 hours after stroke. These experiments suggest that J147 alone fails to provide any significant protection from stoke in the absence of reperfusion (e.g., reperfusion induced by TPA).

Example 6—Prophetic Treatment

A male subject is diagnosed as having a coronavirus infection. The subject is administered a therapeutically effective amount of tPA and is subsequently administered J147 intravenously at a dose of 1 mg/kg, followed by administration of daily i.v. doses of 1 mg/kg continuing for a time period of 1 to 6 weeks. The subject is assessed for DIC, internal hemorrhage and/or respiratory distress. After 3 days the subject is determined to have little or no respiratory distress.

Example 7—Prophetic Treatment

A patient presents in the emergency room with symptoms of coronavirus infection. It is determined that they have a medical history of cardiovascular disease (CVD). It is further determined that the virus infection has caused thrombotic microangiopathy involving the lungs, accompanied by thrombosed small vessels with capillary hyaline thrombi, intravascular mixed thrombi, and significant associated hemorrhages. There is evidence of platelet activation with microcirculation abnormalities implicating blood hypercoagulability. Antithrombotic treatments, such as unfractionated heparin, low-molecular-weight heparins, and direct oral anticoagulants (DOACs) are the first line for management of patients with CVD and coronavirus coagulopathy. Antiplatelet therapy, such as aspirin, clopidogrel, prasugrel and ticagrelor, which are important for secondary prevention of arterial thrombosis, may also be indicated. However, all of these therapies carry a significant risk for causing hemorrhage or exacerbating existing hemorrhages. Intravenous treatment with J147 at a dose of 1-5 mg/kg, followed by administration of daily i.v. doses of 1-5 mg/kg continuing for a time-period of 1 to 6 weeks significantly reduces the risk of hemorrhage and extends the safe and effective range of thrombotic and antiplatelet treatments.

Example 8—Certain Non-Limiting Embodiments

A1. A method of preventing, reducing a risk of, inhibiting, reducing, mitigating or treating a coronavirus infection, coronavirus-induced respiratory distress, coronavirus-induced disseminated intravascular coagulation (DIC) and/or coronavirus-induced vascular instability in a subject, comprising administering to the subject (i) a therapeutically effective amount of a thrombolytic therapy or an anticoagulant, and/or (ii) a therapeutically effective amount of a compound having the structure of Formula I:

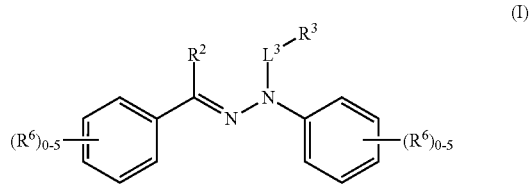

or a pharmaceutically acceptable salt, stereoisomer or tautomer thereof,
wherein:
R$^2$ is selected from the group consisting of H and methyl;
R$^3$ is trifluoromethyl or other fluoro substituted alkyl;
L$^3$ is a carbonyl; and
R$^6$ at each occurrence is independently selected from the group consisting of alkyl, substituted alkyl, cycloalkyl, substituted cycloalkyl, hydroxyl, alkoxy, substituted alkoxy, aryloxy, substituted aryloxy, mercapto, alkylthio, arylthio, carbonyl, aryl, substituted aryl, substituted heterocyclic, halogen, cyano, cyanoalkyl, nitro, amino, amidino, carbamate, S(O)$_n$R$^7$ and C(O)R$^8$ or two R$^6$ at adjacent positions combine to form an optionally substituted heteroaryl or heteroalkyl ring fused with the adjoining phenyl moiety;
R$^7$ is H, R$^9$, NH$_2$, HNR$^9$ or NR$^9$R$^{10}$;
R$^8$ is OH, OR$^9$, NH$_2$, NHR$^9$ or NR$^9$R$^{10}$;
R$^9$ and R$^{10}$ at each occurrence are independently optionally substituted alkyl; and
n=1 or 2.

A2. The method of embodiment A1, wherein R$^6$ at each occurrence is selected from the group consisting of alkyl, substituted alkyl, hydroxyl, alkoxy, substituted alkoxy, halogen, and C(O)R$^8$.

A3. The method of embodiment A2, wherein R$^6$ at each occurrence is selected from the group consisting of methyl, methoxy, perfluoromethyl, perfluoromethoxy, hydroxyl, Cl, F, and I.

A4. The method of embodiment A1, wherein the compound has the structure of Formula II;

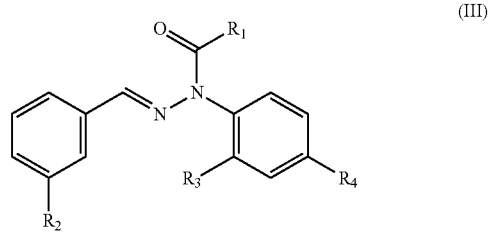

or a pharmaceutically acceptable salt, stereoisomer or tautomer thereof, wherein:
(i) R$^{A2}$, R$^{A4}$, R$^{A5}$, and R$^{A6}$ is H, R$^{A3}$ is methoxy, R$^{B2}$ is methyl, and R$^{B4}$ is methyl; or
(ii) R$^{A2}$, R$^{A3}$, R$^{A5}$, and R$^{A6}$ is H, R$^{A4}$ is methoxy, R$^{B2}$ is methyl, and R$^{B4}$ is methyl; or
(iii) R$^{A2}$, R$^{A3}$, R$^{A4}$, R$^{A5}$, and R$^{A6}$ is H, R$^{B2}$ is H, and R$^{B4}$ is H; or
(iv) R$^{A2}$, R$^{A3}$, R$^{A4}$, R$^{A5}$, and R$^{A6}$ is H, R$^{B2}$ is methyl, and R$^{B4}$ is methyl; or
(v) R$^{A2}$, R$^{A4}$, R$^{A5}$, and R$^{A6}$ is H, R$^{A3}$ is methoxy, R$^{B2}$ is H, and R$^{B4}$ is H; or
(vi) R$^{A2}$, R$^{A3}$, R$^{A4}$, R$^{A5}$, and R$^{A6}$ is H, R$^{B2}$ is H, and R$^{B4}$ is methyl; or
(vii) R$^{A2}$, R$^{A4}$, R$^{A5}$, and R$^{A6}$ is H, R$^{A3}$ is methoxy, R$^{B2}$ is H, and R$^{B4}$ is methyl; or
(viii) R$^{A2}$, R$^{A3}$, R$^{A4}$, R$^{A5}$, and R$^{A6}$ is H, R$^{B2}$ is methyl, and R$^{B4}$ is H; or
(ix) R$^{A2}$, R$^{A4}$, R$^{A5}$, and R$^{A6}$ is H, R$^{A3}$ is methoxy, R$^{B2}$ is methyl, and R$^{B4}$ is H; or
(x) R$^{A2}$, R$^{A3}$, R$^{A5}$, and R$^{A6}$ is H, R$^{A4}$ is COOH, R$^{B2}$ is methyl, and R$^{B4}$ is methyl; or
(xi) R$^{A2}$, R$^{A4}$, and R$^{A5}$ is H, R$^{A3}$ and R$^{A6}$ is hydroxyl, R$^{B2}$ is methyl, and R$^{B4}$ is methyl; or
(xii) R$^{A2}$, R$^{A4}$, and R$^{A6}$ is H, R$^{A3}$ and R$^{A5}$ is hydroxyl, R$^{B2}$ is methyl, and R$^{B4}$ is methyl; or
(xiii) R$^{A2}$, R$^{A4}$, and R$^{A5}$ is H, R$^{A3}$ is methoxy, R$^{A6}$ is F, R$^{B2}$ is H, and R$^{B4}$ is Cl; or
(xiv) R$^{A3}$ and R$^{A5}$ is H, R$^{A2}$ and R$^{A6}$ is F, R$^{A4}$ is hydroxyl, R$^{A6}$ is F, R$^{B2}$ is H, and R$^{B4}$ is F; or
(xv) R$^{A2}$, R$^{A4}$, and R$^{A6}$ is H, R$^{A3}$ is hydroxyl, R$^{A5}$ is F, R$^{B2}$ is H, and R$^{B4}$ is F; or
(xvi) R$^{A2}$, R$^{A5}$, and R$^{A6}$ is H, R$^{A3}$ and R$^{A4}$ taken together are —O—CH2-O—, R$^{A5}$ is F, R$^{B2}$ is H, and R$^{B4}$ is F.

A5. The method of embodiment A4, wherein R$^{A2}$, R$^{A4}$, R$^A$S, and R$^{A6}$ is H, R$^{A3}$ is methoxy, R$^{B2}$ is methyl, and R$^{B4}$ is methyl.

A6. The method of any one of embodiments A1 to A5, wherein the compound comprises a structure of Formula III;

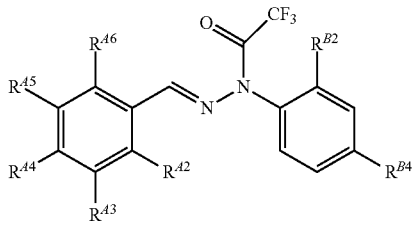

or a pharmaceutically acceptable salt, stereoisomer or tautomer thereof, wherein R$_1$ is methyl, fluoromethyl, difluoromethyl, trifluoromethyl, bromomethyl, dibromomethyl or tribromomethyl; R$_2$ is OCH$_3$, OCF$_3$ or OCBr$_3$; and R$_3$ and R$_4$ are independently selected from hydrogen, hydroxyl, a halogen (e.g., Cl, F or Br), methyl, a methoxy, or an amine.

A7. The method of A1, wherein the compound has the structure of structure selected from any one of Formulas I, II or III, or a pharmaceutically acceptable salt, stereoisomer or tautomer thereof.

A8. The method of A1, wherein the compound has the structure of structure of Formula IV;

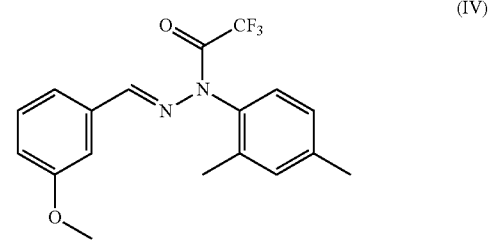 [SMILES: COc1cccc(/C=N/N(C(=O)C(F)(F)F)c2ccc(C)cc2C)c1]

or a pharmaceutically acceptable salt, stereoisomer or tautomer thereof.

A9. The method of any one of embodiments A1 to A8, wherein the subject is human.

A10. The method of any one of embodiments A1 to A9, wherein the subject is elderly or at least 60 years of age.

A11. The method of any one of embodiments A1 to A10, wherein the subject has a clotting disorder.

A11.1 The method of any one of embodiments A1 to A11, wherein the subject has or is suspected of having prothrombotic coagulopathy or one or more blood clots.

A11.2 The method of any one of embodiments A1 to A11, wherein the subject has or presents with coagulopathy or internal hemorrhage.

A12. The method of any one of embodiments A1 to A11, wherein the subject is at risk of being intubated, and/or at risk of being operably connected to a ventilator.

A13. The method of any one of embodiments A1 to A12, wherein the subject is intubated, and/or is operably connected to a ventilator.

A14. The method of any one of embodiments 23 to 26, wherein the respiratory distress is selected from acute respiratory distress, acute respiratory distress syndrome (ARDS), and severe acute respiratory syndrome (SARS).

A15. The method of embodiment A14, wherein the respiratory distress is acute respiratory distress syndrome (ARDS).

A16. The method of any one of embodiments A1 to A15, wherein the subject has or is risk of ARDS or SARS.

A17. The method of any one of embodiment A1 to A16, wherein the coronavirus is SARS-associated coronavirus, SARS-associated coronavirus-2, or a natural variant or strain thereof.

A18. The method of any one of embodiment A1 to A17, wherein the subject is infected with a coronavirus.

A19. The method of embodiment A18, wherein the coronavirus is SARS-CoV, SARS-CoV-2, or a natural variant or strain thereof.

A20. The method of anyone of embodiments A1 to A19, wherein the thrombolytic therapy is administered prior to, during or after administration of the compound.

A21. The method of any one of embodiments A1 to A19, wherein the anticoagulant is administered prior to, during or after administration of the compound.

A22. The method of embodiment A20 or A21, wherein the thrombolytic therapy comprises administration of a tissue plasminogen activator (tPA), a streptokinase, a streptokinase activator or a urokinase.

A23. The method of embodiment A22, wherein the streptokinase activator is an anisoylated plasminogen streptokinase activator complex.

A24. The method of embodiment A23, wherein the anisoylated plasminogen streptokinase activator complex is anistreplase or Eminase.

A25. The method of embodiment A22, wherein the urokinase is a urokinase-type plasminogen activator.

A26. The method of embodiment A25, wherein the urokinase-type plasminogen activator is saruplase.

A27. The method of embodiment A22, wherein the tissue plasminogen activator is a recombinant tPA.

A28. The method of embodiment A22, wherein the tissue plasminogen activator is alteplase (Activase), reteplase (Retavase), or tenecteplase (TNKase, Metalyse).

A29. The method of any one of embodiments A20 to A28, wherein the anticoagulant comprises a vitamin K antagonist.

A30. The method of embodiment A29, wherein the vitamin K antagonist is warfarin.

A31. The method of any one of embodiments A20 to A30, where the anticoagulant comprises heparin, a derivative thereof, or a low molecular weight heparin.

A32. The method of embodiment A31, wherein the derivative of heparin, or the low molecular weight heparin is selected from enoxaparin, dalteparin, tinzaparin and danaparoid.

A33. The method of any one of embodiments A20 to A32, wherein the anticoagulant comprises a thrombin inhibitor.

A34. The method of embodiment A33, wherein the thrombin inhibitor is selected from bivalirudin, argatroban, dabigatran, desirudin, lepirudin and antithrombin III.

A35. The method of any one of embodiments A20 to A34, wherein the anticoagulant comprises a Factor Xa inhibitor.

A36. The method of embodiment A35, wherein the Factor Xa inhibitor is selected from apixaban, fondaparinux, rivaroxaban, edoxaban and betrixaban.

A37. The method of any one of embodiments A1 to A36, wherein the compound is administered prior to, during or after administration of tPA.

A38. The method of any one of embodiments A1 to A37, wherein the compound is administered in combination with tPA treatment.

A39. The method of any one of embodiments A1 to A38, wherein the compound is administered at an interval of once or twice per day.

A40. The method of any one of embodiments A1 to A39, wherein the compound is administered at a dose of 0.5 mg/kg to 100 mg/kg, or 10 mg/kg to 50 mg/kg (wt/wt).

A41. The method of any one of embodiments A1 to A40, wherein the compound is administered orally or intravenously.

A41.1. The method of any one of embodiments A1 to A41, wherein the compound is administered to the subject, or subject at risk, prior to, during, and/or after the subject is intubated or is operably connected to a ventilator.

A42. The method of embodiment A41.1, wherein the compound is administered at least 24 hours, at least 12 hours or at least 4 hours prior to the intubation, or prior to the operable connection to the ventilator.

A43. The method of any one of embodiments A1 to A42, wherein the compound is administered at an interval of once or twice per day.

A44. The method of any one of embodiments A1 to A43, wherein the compound is administered at a dose of 0.5 mg/kg to 100 mg/kg, or 10 mg/kg to 50 mg/kg.

A45. The method of any one of embodiments A1 to A44, wherein the compound is administered orally or intravenously.

A46. The method of any one of embodiments A1 to A45, wherein the compound is administered to the subject prior to, during, and/or after the subject experiences the respiratory distress.

A47. The method of any one of embodiments A1 to A46, wherein the compound is administered at least 24 hours, at least 12 hours or at least 4 hours prior to the onset of the respiratory distress.

A48. The compound having the structure selected from any one of Formula I, Formula II, Formula III and Formula IV for use in conducting the method of any one of embodiments A1 to A47.

A49. A pharmaceutical composition comprising the compound having the structure selected from any one of Formula I, Formula II, Formula III and Formula IV for use in conducting the method of any one of embodiments A1 to A47.

B1. The method of any one of embodiments A1 to A47, wherein the subject has a blood or plasma level of endogenous tPA above 30 ng/ml (wt/vol.), or in a range of 30 ng/ml to 400 ng/ml.

B2. The method of any one of embodiments A1 to A47, or B1, wherein the subject has a blood or plasma level of plasminogen activator inhibitor-1 (PAI-1) above 30 ng/ml, or in range of 30 ng/ml to 400 ng/ml.

B3. The method of any one of embodiments A1 to A47, wherein the subject has a blood or plasma level of endogenous tPA above 30 ng/ml (wt/vol.) and a blood or plasma level of PAI-1 above 30 ng/ml. B4. The method of any one of embodiments A1 to A47, or B3, wherein the subject has a blood or plasma level of endogenous tPA in a range of 30 ng/ml to 400 ng/ml, and a blood or plasma level of PAI-1 in a range of 30 ng/ml to 400 ng/ml.

The entirety of each patent, patent application, publication or any other reference or document cited herein hereby is incorporated by reference. In case of conflict, the specification, including definitions, will control.

Citation of any patent, patent application, publication or any other document is not an admission that any of the foregoing is pertinent prior art, nor does it constitute any admission as to the contents or date of these publications or documents.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

All of the features disclosed herein may be combined in any combination. Each feature disclosed in the specification may be replaced by an alternative feature serving a same, equivalent, or similar purpose. Thus, unless expressly stated otherwise, disclosed features (e.g., antibodies) are an example of a genus of equivalent or similar features.

As used herein, all numerical values or numerical ranges include integers within such ranges and fractions of the values or the integers within ranges unless the context clearly indicates otherwise. Further, when a listing of values is described herein (e.g., about 50%, 60%, 70%, 80%, 85% or 86%) the listing includes all intermediate and fractional values thereof (e.g., 54%, 85.4%). Thus, to illustrate, reference to 80% or more identity, includes 81%, 82%, 83%, 84%, 85%, 86%, 87%, 88%, 89%, 90%, 91%, 92%, 93%, 94% etc., as well as 81.1%, 81.2%, 81.3%, 81.4%, 81.5%, etc., 82.1%, 82.2%, 82.3%, 82.4%, 82.5%, etc., and so forth.

Reference to an integer with more (greater) or less than includes any number greater or less than the reference number, respectively. Thus, for example, a reference to less than 100, includes 99, 98, 97, etc. all the way down to the number one (1); and less than 10, includes 9, 8, 7, etc. all the way down to the number one (1).

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth.

Reference to a series of ranges includes ranges which combine the values of the boundaries of different ranges within the series. Thus, to illustrate reference to a series of ranges, for example, of 1-10, 10-20, 20-30, 30-40, 40-50, 50-60, 60-75, 75-100, 100-150, 150-200, 200-250, 250-300, 300-400, 400-500, 500-750, 750-1,000, 1,000-1,500, 1,500-2,000, 2,000-2,500, 2,500-3,000, 3,000-3,500, 3,500-4,000, 4,000-4,500, 4,500-5,000, 5,500-6,000, 6,000-7,000, 7,000-8,000, or 8,000-9,000, includes ranges of 10-50, 50-100, 100-1,000, 1,000-3,000, 2,000-4,000, etc.

Modifications can be made to the foregoing without departing from the basic aspects of the technology. Although the technology has been described in substantial detail with reference to one or more specific embodiments, those of ordinary skill in the art will recognize that changes can be made to the embodiments specifically disclosed in this application, yet these modifications and improvements are within the scope and spirit of the technology.

The invention is generally disclosed herein using affirmative language to describe the numerous embodiments and aspects. The invention also specifically includes embodiments in which particular subject matter is excluded, in full or in part, such as substances or materials, method steps and conditions, protocols, or procedures. For example, in some embodiments or aspects of the methods disclosed herein, some materials and/or method steps are excluded. Thus, even though the invention is generally not expressed herein in terms of what the invention does not include aspects that are not expressly excluded in the invention are nevertheless disclosed herein.

Some embodiments of the technology described herein suitably can be practiced in the absence of an element not specifically disclosed herein. Accordingly, in some embodiments the term "comprising" or "comprises" can be replaced with "consisting essentially of" or "consisting of" or grammatical variations thereof. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. The term, "substantially" as used herein refers to a value modifier meaning "at least 95%", "at least 96%", "at least 97%", "at least 98%", or "at least 99%" and may include 100%. For example, a composition that is substantially free of X, may include less than 5%, less than 4%, less than 3%, less than 2%, or less than 1% of X, and/or X may be absent or undetectable in the composition.

We claim:

1. A method of reducing a risk of, inhibiting, reducing, or mitigating coronavirus-induced vascular instability in a subject, comprising administering to the subject a therapeutically effective amount of a compound having the structure of Formula IV:

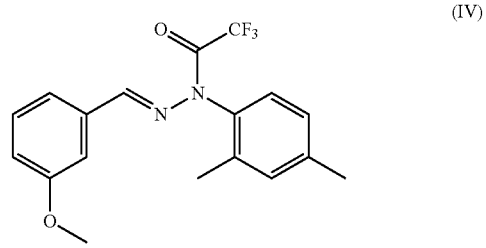 [SMILES: COc1cccc(/C=N/N(C(=O)C(F)(F)F)c2ccc(C)cc2C)c1]

(IV)

or a pharmaceutically acceptable salt, stereoisomer or tautomer thereof.

2. The method of claim 1, further comprising administering a therapeutically effective amount of a thrombolytic therapy or an anticoagulant.

3. The method of claim 2, wherein the thrombolytic therapy comprises administering a therapeutically effective amount of tPA.

\* \* \* \* \*